(12) United States Patent
Natan et al.

(10) Patent No.: US 6,624,886 B2
(45) Date of Patent: Sep. 23, 2003

(54) SERS SUBSTRATES FORMED BY HYDROXYLAMINE SEEDING OF COLLOIDAL METAL NANOPARTICLE MONOLAYERS

(75) Inventors: Michael J. Natan, Los Altos, CA (US); Michael D. Musick, Huntingdon Valley, PA (US); Christine Keating, Lemont, PA (US); Kenneth R. Brown, Park City, UT (US)

(73) Assignee: Surromed, Inc., Mountain View, CA (US)

( * ) Notice: Subject to any disclaimer, the term of this patent is extended or adjusted under 35 U.S.C. 154(b) by 0 days.

(21) Appl. No.: 10/144,611

(22) Filed: May 13, 2002

(65) Prior Publication Data

US 2003/0029274 A1 Feb. 13, 2003

Related U.S. Application Data

(62) Division of application No. 09/728,959, filed on Dec. 4, 2000, now abandoned.
(60) Provisional application No. 60/168,884, filed on Dec. 3, 1999, and provisional application No. 60/168,892, filed on Dec. 3, 1999.

(51) Int. Cl.$^7$ .............................. G01J 3/44; G01N 21/65
(52) U.S. Cl. ........................................ 356/301; 75/741
(58) Field of Search ........................................ 356/301

(56) References Cited

U.S. PATENT DOCUMENTS

| 5,034,313 A | 7/1991 | Shuman |
| 5,609,907 A | 3/1997 | Natan |
| 5,872,013 A | 2/1999 | Leunissen et al. |

FOREIGN PATENT DOCUMENTS

EP  0 426 300 B1  6/1998

OTHER PUBLICATIONS

Bright et al. (1996) Langmuir 12:810–817.
Bright et al. (Jun. 1998) Langmuir 14:5695–5701.
Brown and Natan (1998) Langmuir 14:726–728.
Freeman et al. (Mar. 1995) Science 267:1629–1632.
Goodman et al. (Aug. 1981) J. Microsc. 123:201–213.
Grabar et al. (Feb. 1995) Analytical Chemistry 67:735–743.
Grabar et al. (1997) Anal. Chem. 69:471–477.
Grabar et al. (Feb. 1996) J. Am. Chem. Soc. 118:1148–1153.
Grabar et al. Langmuir 12:2353–2361.
Holland et al. (1999) Chem. Mater. 11:795–805 (pub on web Feb. 19, 1999).
Holland et al. (Jul. 1998) Science 281:538–540.
Horisberger (1979) Biol. Cellulaire 36:253–258.
Keating (Jul. 1999) J. Chem. Educ. 76:949–955.
Lee and Melsel (1982) J. Phys. Chem. 86:3391–3395.
Shipway et al. (1999) Chem. Mater. 11:13–15 (pub on web Dec. 19, 1998).

*Primary Examiner*—F. L. Evans
(74) *Attorney, Agent, or Firm*—Swanson & Bratschun, L.L.C.

(57) ABSTRACT

Methods for preparing colloidal metal nanoparticles, in which seed colloids are added to a solution of reductant mixed with a solution containing a source of metal ions, include a method in which the seeds are colloidal gold nanoparticles, the source of gold ions is $HAuCl_4$, and the reductant is $NH_2OH$. SERS substrates are prepared by combining a colloidal gold monolayer with a solution containing a source of metal ions and a reductant such as $NH_2OH$.

8 Claims, 13 Drawing Sheets

SERS SUBSTRATES FORMED BY HYDROXYLAMINE SEEDING OF COLLOIDAL METAL NANOPARTICLE MONOLAYERS

RELATED APPLICATIONS

This application is a divisional of U.S. patent application Ser. No. 09/728,959, "Hydroxylamine Seeding of Colloidal Metal Nanoparticles," filed Dec. 4, 2000, new abandoned, hereby incorporated herein by reference, which claims the benefit of U.S. Provisional Application No. 60/168,884, "Hydroxylamine Seeding of Colloidal Au Nanoparticles in Solution and on Surface," filed Dec. 3, 1999, and of U.S. Provisional Application No. 60/168,892, "Metal Films Prepared by Stepwise Assembly 2. Construction and Characterization of Colloidal Au and Ag Multilayers," filed Dec. 3, 1999.

FIELD OF THE INVENTION

The present invention relates generally to formation of colloidal metal nanoparticles and films of colloidal metal nanoparticles. In particular, the present invention relates to colloidal metal nanoparticles prepared by hydroxylamine seeding and monolayers of such colloidal metal nanoparticles.

BACKGROUND OF THE INVENTION

The use of nanosized colloidal Au nanoparticles has expanded greatly in recent years. Whereas ten to fifteen years ago, the predominant use of colloidal Au was in biological transmission electron microscopy, a wide variety of recent papers now describe interesting physical properties and possible applications that extend far beyond imaging. For example, colorimetric DNA sensors based on colloidal Au have been developed. Moreover, organized two-dimensional (2-D) and three-dimensional (3-D) arrays of colloidal Au nanoparticles are now occupying the attention of several groups. Unless one studies metal nanoparticles one at a time, as has recently been described, understanding the behavior of solutions and/or surfaces containing Au nanoparticles is predicated upon having a single size (and shape) of particle because, in the nanometer regime, almost every relevant physical property of colloidal Au is size dependent. Photolithography and, more recently, nanosphere lithography have been used to prepare surfaces with highly regular metal features. However, for materials synthesis and for manipulations of these particles in solution, nanoparticles prepared from metal ions in solution are the preferred starting materials.

Many different preparations have been reported for the synthesis of colloidal Au, including even some that begin with bulk metal. However, most such preparations begin with $Au^{3+}$ and, through use of different reductants, generate particles with a range of particle sizes. For example, reducing agents such as $NaBH_4$ or white phosphorous produce small Au particles (diameter <10 nm), while reductants such as ascorbic acid yield colloidal Au nanoparticles with diameters larger than 10 nm. The most widely-studied reductant is sodium citrate; by varying the citrate:Au ratio, it is possible to prepare colloidal particles with diameters (d) ranging from 10–150 nm. Unfortunately, for d>30 nm, the monodispersity becomes poor and the ellipticity (G)—the ratio of the major to minor axis—significantly exceeds unity, the value for a sphere. As a result, these particles are of limited value for nanometer-scale architecture. Indeed, of the many published routes to colloidal Au, none produce large (>50 nm) particles with good monodispersity. Their utility is further restricted by the low particle concentrations generated by these methods. For example, EP 426300B1 describes 2.6-nm diameter colloidal Au nanoparticles ("seeds") prepared by $BH_4^-$ reduction grown to larger sizes by addition of a boiling solution of $HAuCl_4$ and citrate. This approach produces large colloidal Au particles more predictably and reproducibly than citrate reduction, but because the seeds are highly polydisperse (40% standard deviation), the monodispersity is comparable.

Formation of conductive metal films by faradaic and non-faradaic deposition onto immobilized metal nanoparticles is a widely-used process in industry, and of significant recent interest. The focus of this work has typically been on production of thin films exhibiting high conductivity and good adhesion, with special attention given to micron-to-submicron control of film thickness and ease of fabrication. Though largely successful, two aspects of film growth by electroless metal deposition have received little attention. The first is that the number of metal nanoparticles used to nucleate film growth is usually not a controllable parameter. As a result, detailed mechanistic information about particle coalescence is lacking. The second is that the analogous processes in solution—that is, enlargement of suspended metal nanoparticles—have not been studied. As a result, information about the size and shape of growing particles is unavailable.

Accordingly, there remains a need for metal nanoparticles with narrow size distributions, and methods for making them. There also remains a need for methods for controlled growth of nanoparticles in Au colloid monolayers, multilayers, and in solution, along with the control of desired physical characteristics of such monolayers, multilayers, and solutions.

Ensembles of nanoparticles display unique optical and electrical properties that are distinct from their respective bulk properties or simply the average measurement of individual particles. To a large extent, however, bulk material properties (i.e., catalytic, optical, electrical, biocompatibility) are determined by nanoscale features. The ability to tune particle, size, shape, chemical composition, array geometry and linking chemistries provides a flexible platform to manipulate material properties through rational design of the principal components (i.e., metal or semiconductor nanoparticles).

Materials composed from 2-D and 3-D ensembles of nanoparticles are becoming increasingly important in analytical and materials chemistries; indeed, practical applications in nanoelectronic and optoelectronic devices, chemical sensors, and catalysis seem imminent. For example, arrays of crystalline modified polystyrene spheres and suspended ensembles of ligand-coated metal nanoparticles are finding use as vapor phase molecular recognition sensors. Self-organized 2-D nanoparticle superlattices of latex spheres, CdS, CdSe, Au, and Ag structures have been constructed and analyzed. Organized 3-D arrays of nanoparticles with inter- and intra-layer particle registry have been assembled from polystyrene, Ag, CdS, and inorganic oxide nanoparticles. However, with the exception of the inorganic oxides reported by Stein and coworkers, (see Holland, et al., *Chem. Mater.* 1999, 11:795–805; and Holland, et al., *Science* 1998, 281:802–804), no assemblies extend more than a few layers above the substrate and none offer any control over film thickness.

Interest in 2-D metal nanoparticle arrays stems from several unique characteristics: (i) Concentrated solutions of monodispersed Au nanoparticles from 2–100 nm in diameter are easily synthesized. Metal nanoparticles readily adsorb onto appropriately derivatized surfaces. Typically, organosilanes, hyperbranched polymers, or alkylthiols are used to generate arrays with random packing but with a reproducible overall coverage and with a reasonable distribution of interparticle spacing. (ii) Optical properties are a function of particle spacing, size, and composition, easily tailored attributes. (iii) Particles have a high surface area, useful for applications in catalysis, electrochemistry, biomolecule conjugation, and surface-sensitive spectroscopies. In contrast to sol-gel or polymer encapsulation, where the majority of the particle is coupled to the matrix and inaccessible to solution or gas phase chemistry, only a small fraction of an individual particle is in contact with the surface. (iv) Fabrication of patterned collections of nanoparticles has potentially important implications in nanoelectronic device fabrication and biosensing. In this regard, Natan and coworkers have previously characterized Au colloid monolayer synthesis, rate of assembly, thermodynamics, and morphology; extension of assemblies into 3-D architectures may lead to new properties and broadened applications. See Grabar, et al., *Anal. Chem.* 1995, 67:735–743; Grabar, et al., *Langmuir* 1996, 12:2353–2361; Grabar, et al., *J. Am. Chem. Soc.* 1996, 118:1148–1153; Keating, et al., *J. Chem. Educ.* 1999, 76:949–955; and Grabar, et al., *Anal. Chem.* 1997, 69:471–477.

Accordingly, there remains a need for the development of a general methodology for assembling bulk metal-like films directly from solution in a stepwise fashion. The present invention overcomes the limitations of the prior art and further illustrates possible applications in electrochemistry, biosensors, conductive coatings, surface patterning, and optical devices.

SUMMARY OF THE INVENTION

The present invention provides a method for preparing colloidal metal nanoparticles, in which a solution of reductant is added to a boiling solution of a source of metal ion coincidentally with seed colloids. In a preferred embodiment, the colloidal metal nanoparticles are colloidal gold nanoparticles, the source of gold ions is $HAuCl_4$, and the reductant is sodium citrate. The present invention is also directed toward a method for preparing colloidal metal nanoparticles, in which seed colloids are added to a solution of reductant mixed with a solution containing a source of metal ions. In a preferred embodiment, the colloidal metal nanoparticles are colloidal gold nanoparticles, the source of gold ions is $HAuCl_4$, and the reductant is $NH_2OH$. In a further embodiment, the seed colloids are the result of the application of the method, and the source of metal ions and the reductant are added to the seed colloids in an iterative fashion. The present invention is also directed to the colloidal metal nanoparticles that are the product of the application of the above methods. In one embodiment, colloidal metal nanoparticles have a major axis standard deviation of about 14% or less, a minor axis standard deviation of about 14% or less, and an ellipticity <1.5. In another embodiment, colloidal metal nanoparticles have a major axis standard deviation of about 29% or less, a minor axis standard deviation of about 20% or less, and an ellipticity >1.5.

The present invention is also directed toward a method for enlarging immobilized gold nanoparticles using a similar method of immersing an Au colloid monolayer in a solution of reductant, and adding a solution having a source of $Au^{3+}$. The present invention is also directed towards methods for the preparation of thin gold films whose nanostructure can be varied based on the amount of coverage of Au colloid in the monolayer. In the case of a low-coverage Au colloid monolayer, a gold film with features up to about 50 nm tall and about 75 nm wide results. In the case of a high-coverage Au colloid monolayer, a gold film with features about 25 nm tall or less results.

The present invention is also directed toward the gold films prepared by these methods, including a thin Au film having substantially similar conductivity to pure Au, a thin Au film useful as an a cyclic voltammetry electrode, a thin Au film whose nanostructure is indistinguishable from those of granular metal films prepared by evaporation, and having a mean roughness of about 3 nm rms, a thin Au film with increased SERS intensity, and a thin Au film for which a reflectivity vs. excitation angle plot exhibits a pronounced minimum.

DETAILED DESCRIPTION OF THE INVENTION

Figure 1:
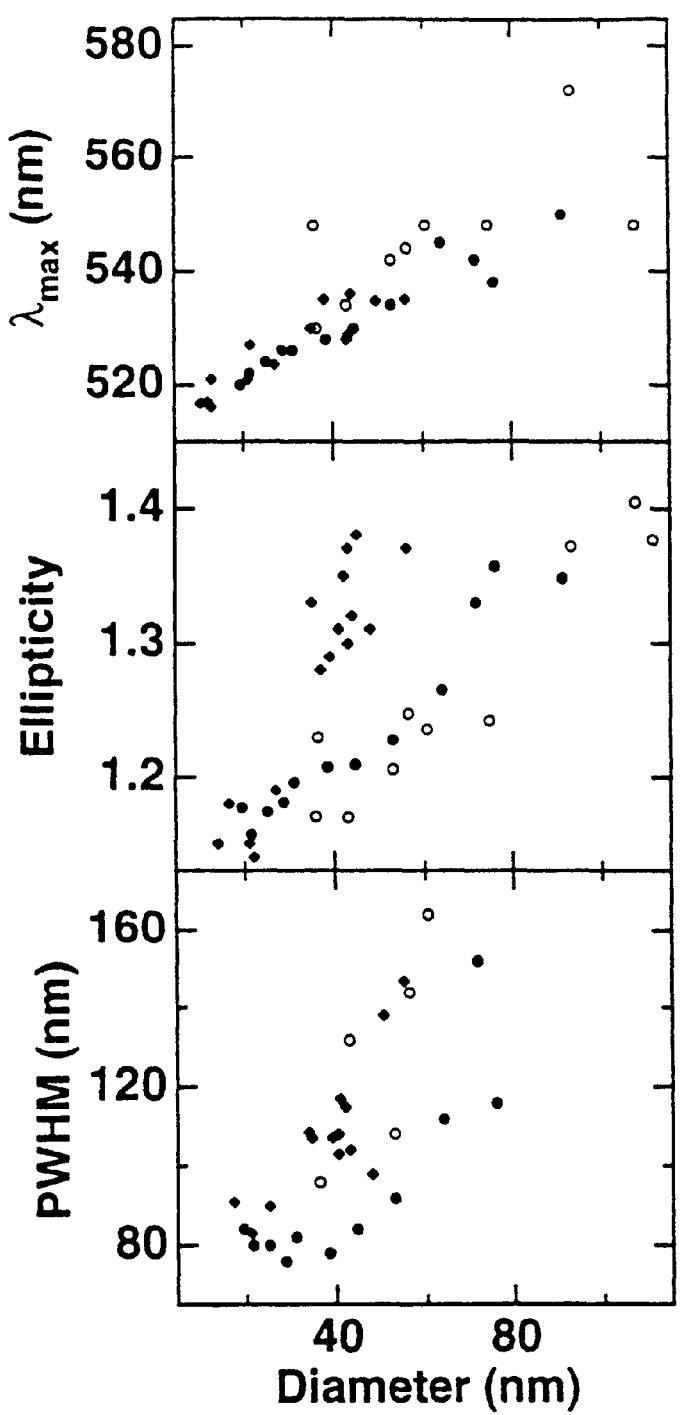
FIG. 1 shows a comparison of $\lambda_{max}$ (top), ellipticity (G) (middle), and peak width at half-max (PWHM) (bottom) versus major axis diameter for colloidal Au nanoparticles prepared by direct citrate reduction of $Au^{3+}$ (♦) and by citrate-based seeding of 2.6-nm diameter (○) and 12-nm diameter (●) colloidal Au.

Many of the examples and embodiments herein describe the use of colloidal Au nanoparticles, but it is to be understood that any other metal (including alloys and mixtures of metals) is also contemplated by and within the scope of the invention. For example, metals include but are not limited to Ag, Cu, Al, or alloys comprised of two or more of Au, Al, Ag, and Cu. In other embodiments, the metal nanoparticles comprise a core of Ag, Al, Au, or Cu (or an alloy of two or more of these metals) substantially covered by a shell of any metal, any oxide, any sulfide, any phosphide, or any organic or inorganic polymer. In addition, although preferred embodiments employ metal nanoparticles that are substantially spherical, it is to be understood that other shapes are also contemplated. Additionally, the glass used may be of any type. Examples of suitable glasses include, but are not limited to SF11 glass slides (Schott Glass Technologies), BK7 microscope slides (Fisher Scientific), and glass cover-slips (Fisher Scientific).

Control of Particle Size and Shape by Seeding of Colloidal Au Nanoparticle Solutions The use of more monodisperse seeds (e.g. 12±1.5 nM diameter) in the present invention yields larger particles and particles with narrower size distributions than those produced by prior art methods. In the present invention, a new synthetic protocol is provided, based on room-temperature seeding of colloidal Au by NH$_2$OH/Au$^{3+}$. This method is consistent and reproducible enough to predict, a priori, final colloidal diameters within a few nanometers. Iterative seeding using this approach can be used to rapidly produce large colloidal Au nanoparticle solutions that exhibit excellent monodispersity. Interestingly, repetitive seeding with NH$_2$OH leads to formation of a small percentage of cylindrical, high aspect-ratio rods. Note that such rods have been generated electrochemically in the pores of membranes.

The present invention includes the preparation and characterization of conductive Au films prepared by controlled growth of the nanoparticles in Au colloid monolayers and multilayers using aqueous solutions of NH$_2$OH/HAuCl$_4$. Formation of conductive metal films by faradaic and non-faradaic deposition onto immobilized metal nanoparticles is a widely-used process in industry.

NH$_2$OH-mediated reduction of Au$^{3+}$ is an excellent route to enlargement of immobilized 12-nm diameter colloidal Au nanoparticles tethered to organosilane-coated glass substrates. By using low concentrations of Au$^{3+}$ (added as HAuCl$_4$), it is possible to monitor and control the rate of particle growth and coalescence. Immersion of Au colloid monolayers for just a few minutes into a shaken flask containing 0.01% HAuCl$_4$/0.4 mM NH$_2$OH leads to evolution of optical properties very similar to those of evaporated Au films near the insulator-conductor threshold; additional exposure leads to metallic thin films with DC resistances as low as 1–10 Ω, allowing them to be used for cyclic voltammetric measurements. Investigation of film nanostructure using atomic force microscopy (AFM) and field-emission scanning electron microscopy (FE-SEM) indicates that enlarged particles are neither spherical nor cylindrical, but rather have a highly complex shape. Not surprisingly, NH$_2$OH-mediated particle enlargement leads to dramatic improvements in SERS enhancement factors. Nanoscale morphology of conductive films depends critically on the initial coverage of 12-nm diameter Au nanoparticles, and SPR measurements are acutely sensitive to such differences, even in films exhibiting ostensibly identical bulk optical and electrical properties.

Particle seeding appears to be a valuable addition to the synthetic repertoire for colloidal Au, both for the production of large particles with improved monodispersity and for fabrication of high-aspect ratio colloidal Au rods. Both boiling citrate and room-temperature hydroxylamine serve effectively as reductants for 2.6- and 12-nm diameter colloidal Au seeds. For hydroxylamine, iterative seeding can be used to grow (from 12-nm diameter seeds) particles with 100–200 nm major axes.

As part of a study aimed at preparation of protein:Au colloid complexes, a thorough study of the physical properties Au nanoparticles made by the Frens method (i.e. direct reduction of Au$^{3+}$ by citrate) has been published; Goodman et al., *J. Microsc.* 1981, 123:201–13; Faulk et al., *Immunochem.* 1971, 8:1081–83; Horisberger, *Biol. Cell.* 1979, 36:253–58; Hayat, Ed., *Colloidal Gold; Principles, Methods, and Applications*; Academic Press: San Diego, 1989, vol. 1-2; Beesley, *Colloidal Gold: A New Perspective for Cytochemical Marking*; Oxford University: Oxford, 1989; Vol. 17; each specifically incorporated by reference. By varying the citrate:$Au^{3+}$ ratio, Au nanoparticles with diameters from 10–70 nm were prepared and characterized by TEM and UV-Vis spectrophotometry. Four parameters were used to describe each preparation of colloid: the wavelength of maximum absorbance ($\lambda_{max}$) and peak width at half max (PWHM) from the UV-Vis data, and the mean particle diameter (d) and ellipticity (G) from TEM data. Due to the asymmetry of the colloidal Au surface plasmon band, PWHM is defined straightforwardly as twice the difference between $\lambda_{max}$ and the $\lambda$ of half-maximal absorbance to the red of the $\lambda_{max}$.

In contrast, the mean particle diameter d is an oversimplification in that no colloidal Au particles are purely spherical: TEM images show the presence of major and minor axes (the ellipticity G is the ratio major:minor axial ratio). Accordingly, while d is used herein in reference to the dimensions of the major axis, all particles are described by mean major and minor axes (e.g. Table 1). The TEM images only two of the three dimensions in a particle, and it is assumed that the dimensions of the third are the same as one of the two imaged. The particles may also be prolate (cigar-shaped; third axis=minor) or oblate (pancake-shaped; third axis=major). While Goodman, et al., *J. Microsc.* 1981, 123:201–13, state that colloidal Au nanoparticles are oblate, both logic and experiment suggest that the reverse is true: particles on TEM grids adsorb so as to maximize their contact with the surface, meaning the axis normal to the surface must be minor. Since minor and major axes are seen in TEM images, there must be two minor axes, making the particles prolate. In accord with this reasoning, atomic force microscopy images of Au nanoparticles on glass slides known to have axes of 40 and 30 μm indicates the tops of the particles are 30 nm above the surface.

The d, G, $\lambda_{max}$, and PWHM for Au nanoparticles made by the Frens method have been compared to those prepared by seeding (FIG. 1 and Table 1).

In the approach described in EP 426300B1, the dimensions of existing Au nanoparticles (the "seeds") are increased by mixing with additional reductant (i.e. citrate) and $Au^{3+}$. In practice, a mixture of citrate and colloidal Au is added to a solution of boiling, dilute $HAuCl_4$ in $H_2O$. What is important for this method is the relative rate of new particle formation (via $Au^{3+}$ reduction) in solution versus the rate of $Au^{3+}$ reduction on the surface of existing particles. If the latter is much greater than the former, then particle growth will occur at the expense of new particle nucleation. From previous work, it is well-appreciated that reduction of $Au^{3+}$ on any small particles is rapid, explaining the need for filtered solutions and scrupulously clean glassware for the production of colloidal Au. New particle nucleation can be therefore be averted by seeding. The absence of new particle nucleation is especially critical for growth of large particles, because in the Frens method, as particles are growing larger, new (small) particles can be forming.

Figure 2:
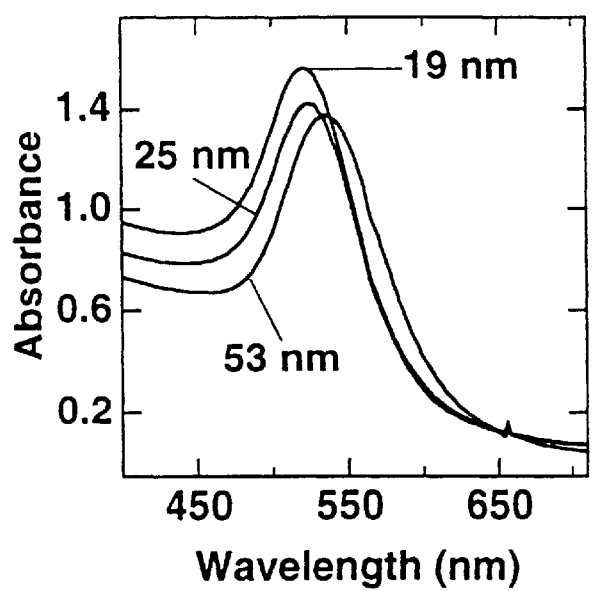
FIG. 2 shows optical spectra for solutions of 19-, 25-, and 53-nm diameter Au nanoparticles grown by citrate seeding of 12-nm diameter colloidal Au. Size and shape data for these particles are described in Table 1.

Several trends are seen in the plots of $\lambda_{max}$, ellipticity, and peak width at half maximum (PWHM) versus particle diameter for colloidal Au made by Frens' method and by seeding using 2.6-nm diameter and 12-nm diameter seeds (FIG. 1). For each type of particle, $\lambda_{max}$ increases with increasing size, although not dramatically. Increasing the diameter of a colloidal Au nanoparticle from 19 nm to 53 nm, nearly a factor of three, leads only to a 14-nm red shift in $\lambda_{max}$ (FIG. 2); red shifts of 150 nm or more can be realized by aggregation of small particles; however, increasing particle diameters lead to increasing ellipticities and to significantly broadened optical spectra. The latter has been shown to result in large part from Rayleigh light scattering from particles with diameters >$\lambda$/20. It should be noted that because light scattering is so sensitive to particle diameter, PWHM can be used as a rapid diagnostic for the quality of citrate-derived, small diameter colloidal Au preparations. For example, preparations of 12-nm diameter colloidal Au with PWHM>85 nm invariably exhibit roughly twofold higher standard deviations in d than those with PWHM<85 nm.

Comparison of the physical properties of colloidal Au prepared by seeding with that made by direct citrate reduction indicates the superiority of the former (Table 1). In particular, G is significantly greater for colloidal Au made by direct citrate reduction: several batches clustered around d=40 nm all had G≧1.3, while the analogous particles made by seeding exhibited G values≈1.2. Even particles in the 20–30 nm diameter range made by direct citrate reduction were more elliptical than the corresponding seeded particles. Moreover, PWHM for seeded particles are consistently lower than for particles made by direct citrate reduction. For the three sizes of 12-nm seeded particles shown in FIG. 2, the PWHM are nearly identical, and the only significant difference is the aforementioned shift in $\lambda_{max}$. Colloidal Au solutions made by direct citrate reduction exhibit broadened PWHM over the entire range of particle diameters.

In theory, the high degree of ellipticity in colloidal Au made by direct citrate reduction arises from two components: differential reduction rates at sites on the particle, and differential diffusion to parts of the particles. High-resolution TEM studies have shown the presence of crystalline faces in small colloidal Au nanoparticles. If reduction of $Au^{3+}$ is substantially faster (or slower) on certain faces than on others, then anisotropic particle growth will occur. In this regard, Weisner & Wokaun, *Chem. Phys. Lett.* 1989, 157:569–75, have shown that under certain conditions, highly anisotropic colloidal Au nanoparticles can be prepared; likewise, production of cubic colloidal particles has also been described. Another factor that could favor elliptical particles is the enhanced amount of $Au^{3+}$ reaching the ends of the ellipse: flux to a hemisphere is enhanced relative to flux to a plane. While this factor is more important in unstirred solutions, even in stirred solutions it could contribute to increased growth at the hemispherical "ends" of a prolate spheroidal particle.

The standard deviations of the axial dimensions are substantially lower for particles seeded with 12-nm diameter colloidal Au than for particles made by direct citrate reduction or 2.6-nm diameter seeding. For example, in batch number 9 of the particles made by direct citrate reduction (Table 1), the major axis is 56±8.4 nm. For small seeds of the corresponding size (batch number 5) d=56±7.2 nm, while for batch number 8 of the large seeds, d=53±4.8 nm. The lower dispersity in particle size for 12-nm seeded particles becomes even more significant for larger particles (e.g., large seed batch number 9 vs. small seed batch number 6, large seed batch number 10 vs. small seed batch number 7).

The increased dispersity in particle size for particles made using 2.6-nm diameter seeds reflects the poor monodispersity and increased ellipticity of the seeds themselves (Table 1). The 2.6-nm diameter colloidal particles have ≈1-nm standard deviations in diameter. While this is about the same absolute standard deviation in diameter measured for good preparations of 12-nm diameter particles, it is quite large as a percentage of particle size. Furthermore, the measured ellipticity is 1.3 (versus 1.1 for 12-nm diameter particles). Accordingly, seeding with 2.6-nm particles leads to more dispersion in particle size, reflected by larger standard deviations in diameter and by very substantial increases in peak widths (Table 1).

In short, citrate seeding 12-nm diameter colloidal Au nanoparticles yields sols with improved physical properties relative to direct particle production by citrate reduction of $Au^{3+}$ or by seeding with 2.6-nm diameter seeds. The disparity in quality of colloidal preparations is especially prevalent for d>40 nm.

Hydroxylamine Seeding

Drawbacks of citrate seeding include the need for boiling $H_2O$ and the need to keep the $Au^{3+}$ and the reductant apart; ideally, seeding could be carried out at room temperature, and initiated upon introduction of seeds to premixed solutions of $Au^{3+}$ and reductant (or introduction of $Au^{3+}$ to a mixture of reductant and seeds). This can be accomplished by a process with a solution nucleation rate constant of zero at room temperature and a surface nucleation rate constant significantly greater than zero at room temperature. In Au electroless metal plating, these requirements are satisfied by chelation of $Au^+$ to cyanide, which moves the solution reduction potential too far negative for formation of AuO, so that only adsorbed $Au^+$ ions is possible. Similarly, the reductant hydroxylamine ($NH_2OH$) has been shown to favor reduction of Au ions at metallic Au surfaces at room temperature over reduction in solution, and the application of $NH_2OH$ seeding to colloidal Au nanoparticles has been described in a preliminary fashion in a preliminary fashion in Brown & Natan, *Langmuir* 1998, 14:726–728.

At room temperature, mixtures of $NH_2OH$ and $Au^{3+}$ (added as $HAuCl_4$) do not lead to formation of colloidal Au nanoparticles in solution. Thus, the optical spectrum of a mixture of 0.01% $HAuCl_4$ and 40 mM $H_2NOH$ is featureless after 20 minutes (spectrum a of FIG. 3). Addition of 50 µl of a solution containing 12-nm diameter colloidal Au seeds leads immediately to significant growth in the intensity of the colloidal Au surface plasmon band (spectra b-e in FIG. 3). Changes in the optical spectra are essentially complete after 11 seconds, since a spectrum recorded after 56 seconds is essentially identical, as are spectra recorded every five seconds between these times (data not shown). Since the formation of new particles is precluded by the control experiment described by spectrum a, the spectral changes suggest enlargement of the seed particles. If so, cessation in particle growth must result from depletion of $Au^{3+}$.

Figure 4:
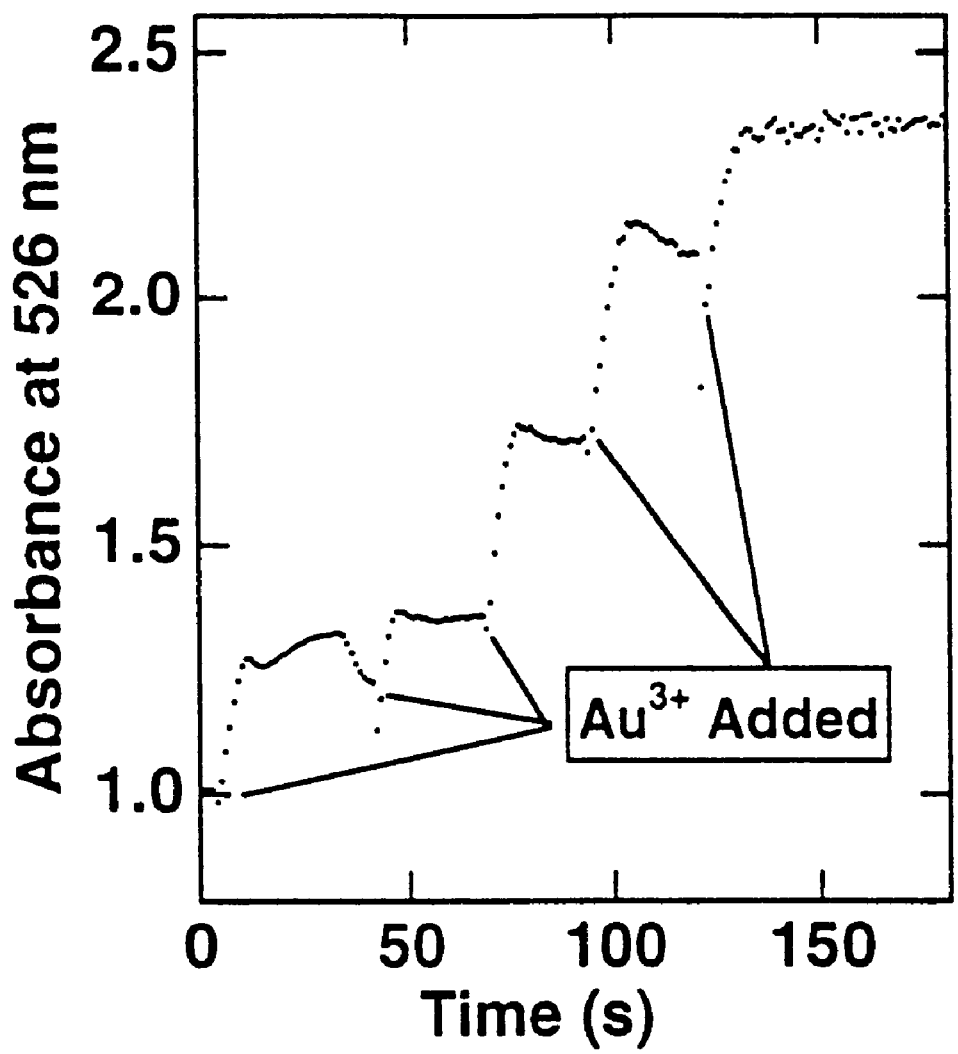
FIG. 4 shows absorbance at 526 nm measured every second (0.1-s integration time) after additions of 0.1 ml of 0.1% $HAuCl_4$ (at the times indicated) to an unstirred mixture of 3.2 ml of 0.01% $HAuCl_4$/0.1 ml of 40 mM $H_2NOH$/0.050 ml of 17 nM, 12-nm diameter colloidal Au.

This notion is confirmed by the data in FIG. 4, which plots the absorbance at 526 nm over time as aliquots of $HAuCl_4$ are added to a pre-reacted mixture of 0.01% $HAuCl_4$, $NH_2OH$, and 12-nm diameter colloidal Au. At t=0, the absorbance A≈1, indicating that the $Au^{3+}$ already in solution has already been consumed to enlarge the 12-nm diameter colloidal Au particles. After addition of $Au^{3+}$, there is a nearly instantaneous increase in absorbance, followed by a slight decrease and then a leveling off. Each subsequent addition of $Au^{3+}$ leads to an increase in absorbance, and to a new (higher) level. Thus, $HAuCl_4$ can be made the limiting reagent in $NH_2OH$-seeded growth of 12-nm diameter colloidal Au: introduction of a known quantity of $Au^{3+}$ to a solution containing colloidal Au nanoparticles and an excess of $NH_2OH$ leads to particle growth, until the $Au^{3+}$ is consumed.

This method of seeded particle growth is valuable in three respects. First, particle enlargement can be carried out at room temperature. Second, since $Au^{3+}$ can be made limiting, particles may be grown to a pre-specified size. Finally, $NH_2OH/Au^{3+}$ seeding is well-suited for growth of immobilized Au nanoparticles, because a colloidal Au-derivatized surface can be easily immersed into a solution of $HAuCl_4/NH_2OH$.

Figure 3:
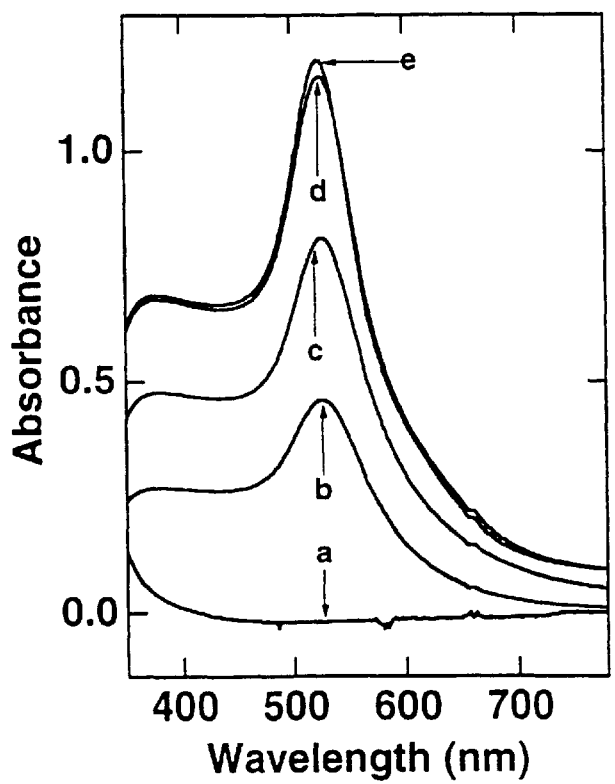
FIG. 3 shows optical spectra (0.1-s integration time) of a mixture of 3.2 ml of 0.01% $HAuCl_4$/0.1 ml of 40 mM $H_2NOH$ after 20 minutes (a), and 1 (b), 6 (c), 11 (d) and 56 seconds (e) after addition (without stirring) of 0.050 ml of 17 nM, 12-nm diameter colloidal Au.

A TEM image of colloidal particles produced by a $NH_2OH/Au^{3+}$ seeding procedure analogous to that described for the data in FIG. 3 was obtained. Two aspects of the image are notable: the excellent monodispersity of the spherical particles (51±5.2 nm×46±4.7 nm), and the presence of a distinct population (5–10%) of colloidal Au rods (141±38 nm×31±4.6 nm) with ellipticities far greater (≈4.5) than any particles derived from citrate reduction of $Au^{3+}$, whether seeded or not. The standard deviation of the major and minor axes of the spherical particles appears equivalent to that produced by citrate seeding with 12-nm diameter colloidal Au. In contrast, the length of the rods' major axis is highly variable, ranging from 90 nm to >200 nm, while the rods' minor axes shows the same small standard deviation (4.7 nm) as the spherical particles. More importantly, the minor axis is more than three standard deviations shorter than the minor axis of the dominant population, suggesting that the rods do not form by fusion of spheres.

Iterative, stepwise seeding favorably impacts the size and shape distribution of the spherical particles. FIG. 1 and Table 1 show clearly that single-step enlargement of 2.6-nm or 12-nm diameter colloidal Au particles diameters below 40 nm is well-behaved; for larger particles, the PWHM and ellipticity seem to rise exponentially. Growing large particles in multiple steps leads to minimization of these effects.

Figure 5:
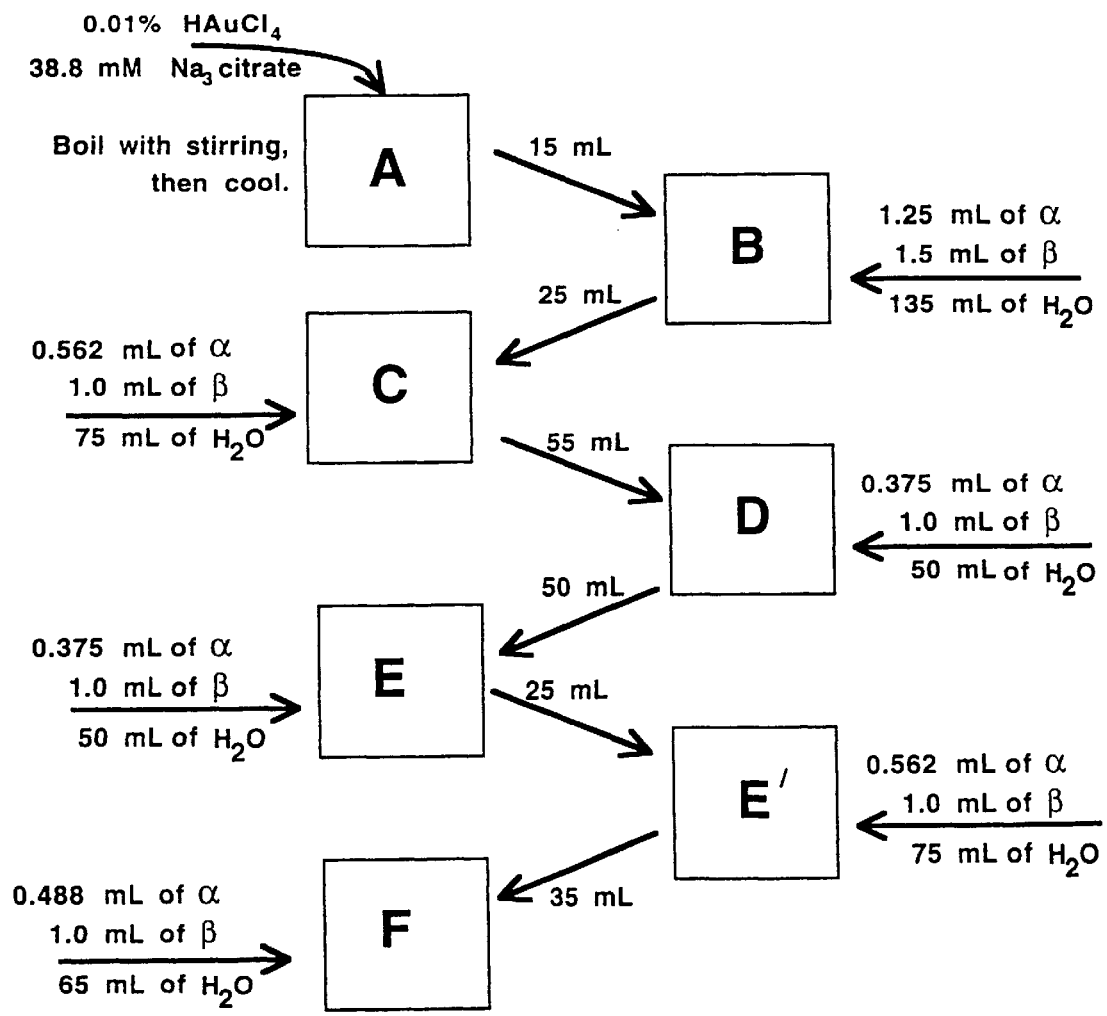
FIG. 5 shows the process of iterative seeding used to produce the colloids discussed in Table 2. The initial colloid batch (A) was prepared by mixing boiling gold (111) with sodium citrate. Reagent α is 0.2 M $H_2NOH$ and reagent β is 1.0% $HAuCl_4$. All subsequent colloids were made by mixing α with colloid in the water and adding β to initiate the reaction. For example, 135 ml water, 1.5 ml of α and 15 ml of colloid A were stirred, and 1.25 ml of reagent β was added while the solution was stirred vigorously at room temperature.
Figure 6:
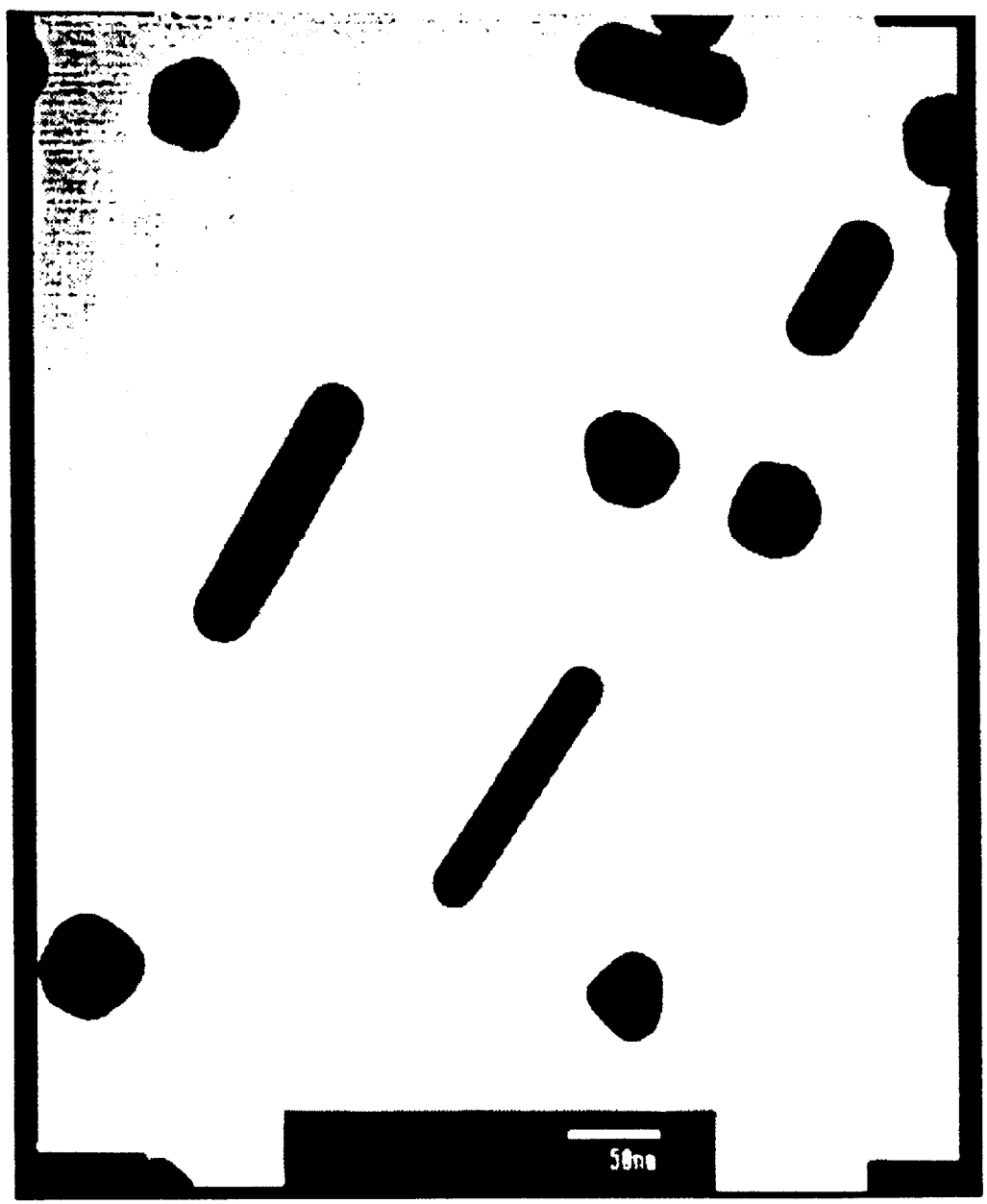
FIG. 6 is an enlarged TEM image of 4th-iteration $NH_2OH$-seeded colloidal Au (panel E in FIG. 6).

The results of an iterative seeding experiment as performed in FIG. 5 are described in Table 2, which gives a detailed particle size analysis. Spherical particles spanning nearly an order of magnitude in size (12–13 nm to over 100 nm) resulted. Colloidal Au rods are definitely not fused or aggregated spheres. This is easily confirmed by examination of FIG. 6, which shows that the rods are solid and are significantly smaller in the minor axis than surrounding quasi-spherical particles. Another interesting point that can be gleaned from FIG. 6 is that none of the rods are blunt-ended: both ends are hemispherical, some almost perfectly so. The second clear finding is that there is no continuum from spherical to rod-shaped particles; rather, there are two distinct populations, with nothing in between. In an exemplary population, the transition from G<1.5 to G>1.5 is extremely abrupt, with a two order-of-magnitude difference in particle populations. In one example where particles had a mean diameter of 41 nm, early 3000 of 3300 particles had a G close to 1, and the remainder had G values from 2 to as high as 8.

Table 2 gives size statistics for both particle shapes individually and for the total set of particles, from which several key points are revealed. (i) Comparison of the median and mean values is provided to show that for samples containing a bimodal sample distribution, the statistical mean differs from the median value of the set. Likewise, the proximity of the median and mean values in small colloidal particle sets demonstrate that in a uniform particle set these two values should be close. (ii) The standard deviation (SD) of the axial dimensions also climbs very quickly. Once the rods are dropped from consideration, the SD for the remaining population drops dramatically and the median and mean values come into close agreement. (iii) Neither the 12 nm or the next larger colloid shows evidence of colloids with high G; the dominant population is spherical. However, the minor axis of the rods is substantially smaller than the minor axis of spheres in the same batch. Thus, the growth of 12 nm seed particles into rods must be a process that is not simply limited to an accelerated growth in one dimension but a reduced growth rate in the other two axial directions.

Given that suspensions of large (>50 nm diameter) Au nanoparticles could be prepared by seeding of pre-formed, 12 nm diameter colloidal Au solutions with $Au^{3+}$ and $NH_2OH$ in solution, the same reaction was performed with immobilized Au colloid monolayers and multilayers, with three synthetic goals. (i) Theory predicts that large-diameter colloidal Au particles are more active for surface enhanced Raman scattering (SERS) than smaller ones; however, in current approaches to SERS-active substrates based on self-assembly colloidal Au or Ag particles from solution, only low concentrations of large Au nanoparticles can be stably prepared, and the diffusion coefficient is inversely proportional to the particle radius. Thus, manufacture of SERS substrates by self-assembly of, e.g., 50-nm diameter colloidal Au particles is laborious. (ii) The insulator-conductor transition in discontinuous or semi-continuous Au thin films prepared by evaporation is of fundamental interest and has been investigated continuously for almost twenty years. Unfortunately, evaporation affords little control of structure on the nanometer scale. Controlled enlargement of a two-dimensional (2-D) array of single-sized Au nanoparticles leads to well-defined 2-D conductors. (iii) Finally, solution fabrication of thin Au films may be well-suited for surface plasmon resonance (SPR). Detection of biomolecular complex formation and/or dissociation using SPR is becoming common. The phenomenon is based on changes in reflectivity of ≈50 nm diameter Au films coated with 200-nm thick films of carboxylated dextrans.

Controlled Formation of Conductive Au Films by Seeding of Colloidal Au Nanoparticle Solutions Bulk Optical and Electrical Properties Based on the results of seeding of colloidal Au nanoparticles with $Au^{3+}/NH_2OH$ in solution, it was anticipated that enlargement of surface-confined particles would proceed as shown in FIG. 5. Starting with a Au colloid monolayer with ≈20% of close-packing coverage, immersion into the seeding solution leads to particle growth. It was expected that the particles will not move (a consequence of several hundred bonds between colloidal Au surface and either —$NH_2$ or —SH groups on the organosilane), and that (at least at early stages of growth), the particles would retain their spherical character.

Figure 7:
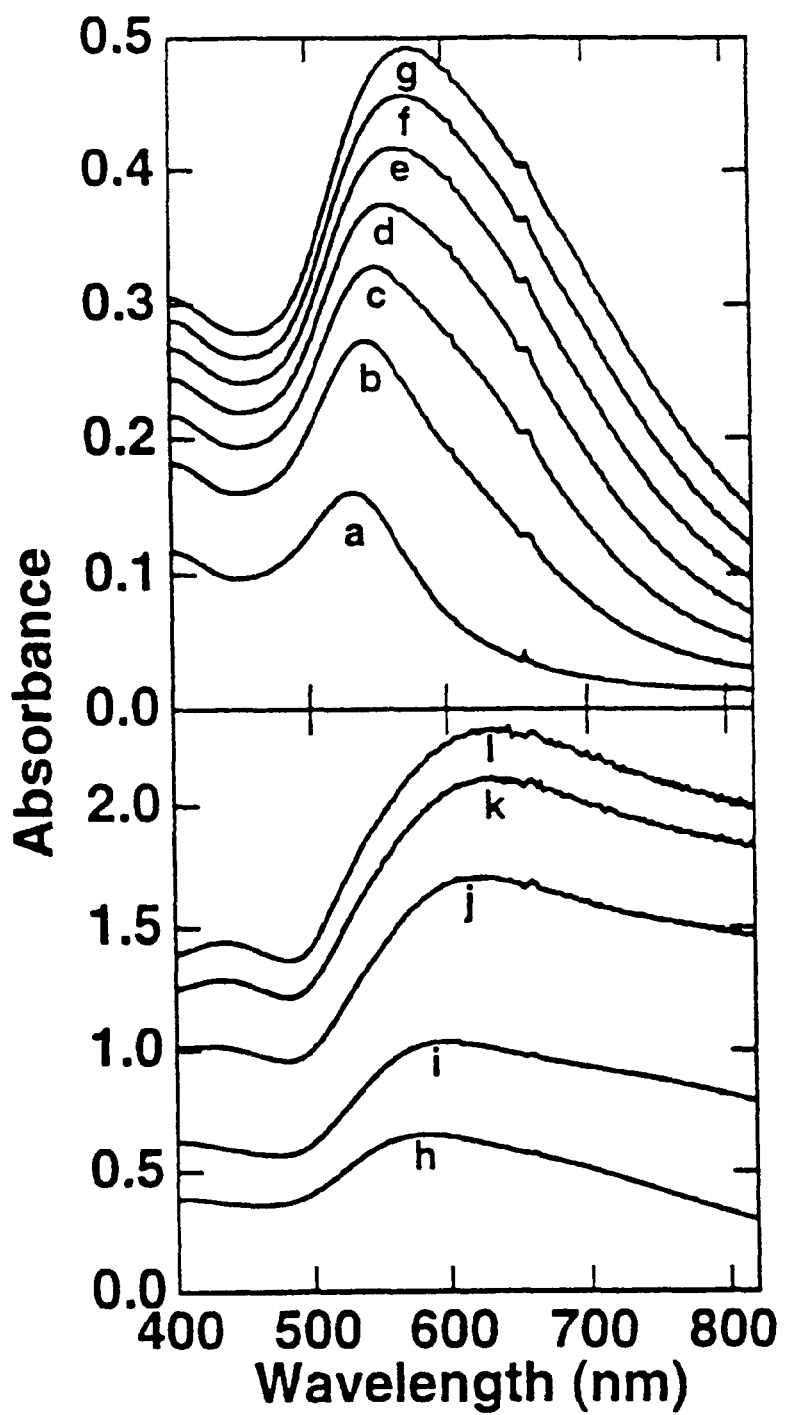
FIG. 7 shows optical spectra in $H_2O$ of a 12-nm diameter Au colloid monolayer on APTMS-coated glass as prepared (a), and after immersion in 0.01 $HAuCl_4$/4 mM $NH_2OH$ for 10 (b), 20 (c), 30 (d), 40 (e), 50 (f), 60 (g), 120 (h), 300 (i), 900 (j), 1500 (k), and 2700 seconds (l).

FIG. 7 shows visible optical spectra over time for a 12-nm Au colloid monolayer on APTMS-coated glass substrate upon immersion in a solution of 0.01% $HAuCl_4$/4 mM $NH_2OH$. Every ten seconds for the first minute (top panel), the absorbance continually increases from the initial colloidal Au monolayer (a). In this time frame there is a noticeable increase in total absorbance but the spectral peak near 520 nm is still clearly defined, albeit slightly red-shifted. As previously discussed, the increased extinction and the shift of $\lambda_{max}$ to longer wavelengths are both consistent with increased dimensions for the particles being interrogated. As time progresses towards 45 minutes of immersion (bottom panel), extinction of light is large over the entire visible spectrum, including at 526 nm, the position of $\lambda_{max}$ for the monolayer. At longer times, the absorption band broadens considerably and $\lambda_{max}$ gradually shifts past 600 nm.

Figure 8:
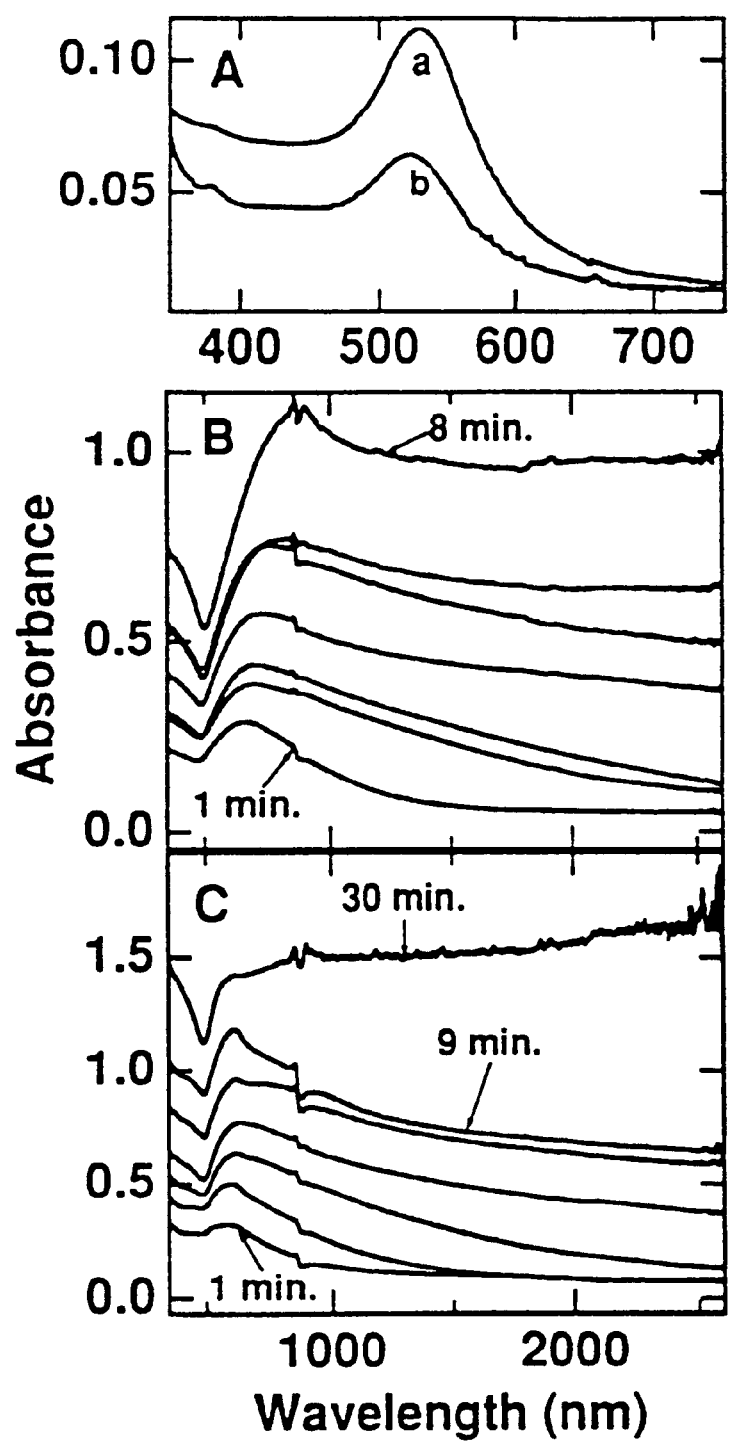
FIG. 8 in the top panel shows representative optical spectra for 12-nm diameter Au colloid monolayers on APTMS- (a) and MPTMS-coated glass (b). The middle panel shows UV-Vis-near-IR spectra for seven 12-nm diameter Au colloid monolayers on APTMS/glass after exposure from 1 to 8 minutes to 0.01% $HAuCl_4$/0.4 mM $NH_2OH$. The bottom panel shows UV-Vis-near-IR spectra for seven 12-nm diameter Au colloid monolayers on MPTMS/glass after exposure from 1 to 30 minutes to 0.01% $HAuCl_4$/0.4 mM $NH_2OH$.

The increase in absorbance accompanying deposition of $Au^\circ$ onto immobilized colloidal particles extends well into the infrared region of the spectrum. The top panel of FIG. 8 shows representative optical spectra from two sets ("high" coverage (a) and "low" coverage (b)) of twenty Au colloid monolayers each from which thin Au films were grown by $Au^{3+}/NH_2OH$ seeding. The middle and bottom panels show near-infrared absorbance over time for Au films grown from colloidal Au monolayers with high and low coverages, respectively. As expected, the absorbance of the low coverage films lags behind that of the high coverage. For example, after 9 minutes of seeding, the low-coverage sample had an absorbance about 20–25% lower than high-coverage sample exhibited after 8 minutes.

Although these surfaces contain only a single layer of particles, as opposed to the numerous strata of spacer-linked colloidal Au in multilayers, they nevertheless exhibit similar near-IR optical spectra. In both cases, increased quantities of Au immobilization lead to decreased transmission and to a loss of wavelength sensitivity. These properties have been observed in percolating Au films prepared by evaporation, with one significant difference: in the latter, the percolation threshold (i.e. the inflection point in insulator-conductor transition) is denoted by the point at which the absorbance becomes wavelength-independent. Here, well before the plots of near-IR absorbance vs. wavelength become horizontal, the Au films are very highly conductive; however, evaporated Au films and high-coverage $NH_2OH$-seeded films do share the attribute of increased absorbance at increasing wavelengths (i.e., an upward-sloping line) in the fully metallic regime. Table 3 lists resistance measurements for enlarged low-coverage and high-coverage Au colloid monolayers.

It is clear that bulk properties are reached more rapidly from high coverage surfaces. For example, after six minutes, the resistance of the high-coverage seeded surface is 1/40, 000th that of the low-coverage seeded surface (14 Ω vs. 650,000 Ω). Conversion of measured resistances into resistivities by accounting for measurement geometry) indicates that both seeded films ultimately achieve extraordinarily high conductivies; for low-coverage colloidal Au monolayers immersed in seeding solution for 30 minutes, the resistivity $\rho=1.0\times10^{-5}$ Ω-cm, in comparison with $2.44\times10^{-6}$ Ω-cm for pure Au at room temperature. Thus, these films are within a factor of four of the conductivity of pure Au (of the same thickness), and far exceed the conductivities for a variety of other metals.

Figure 9:
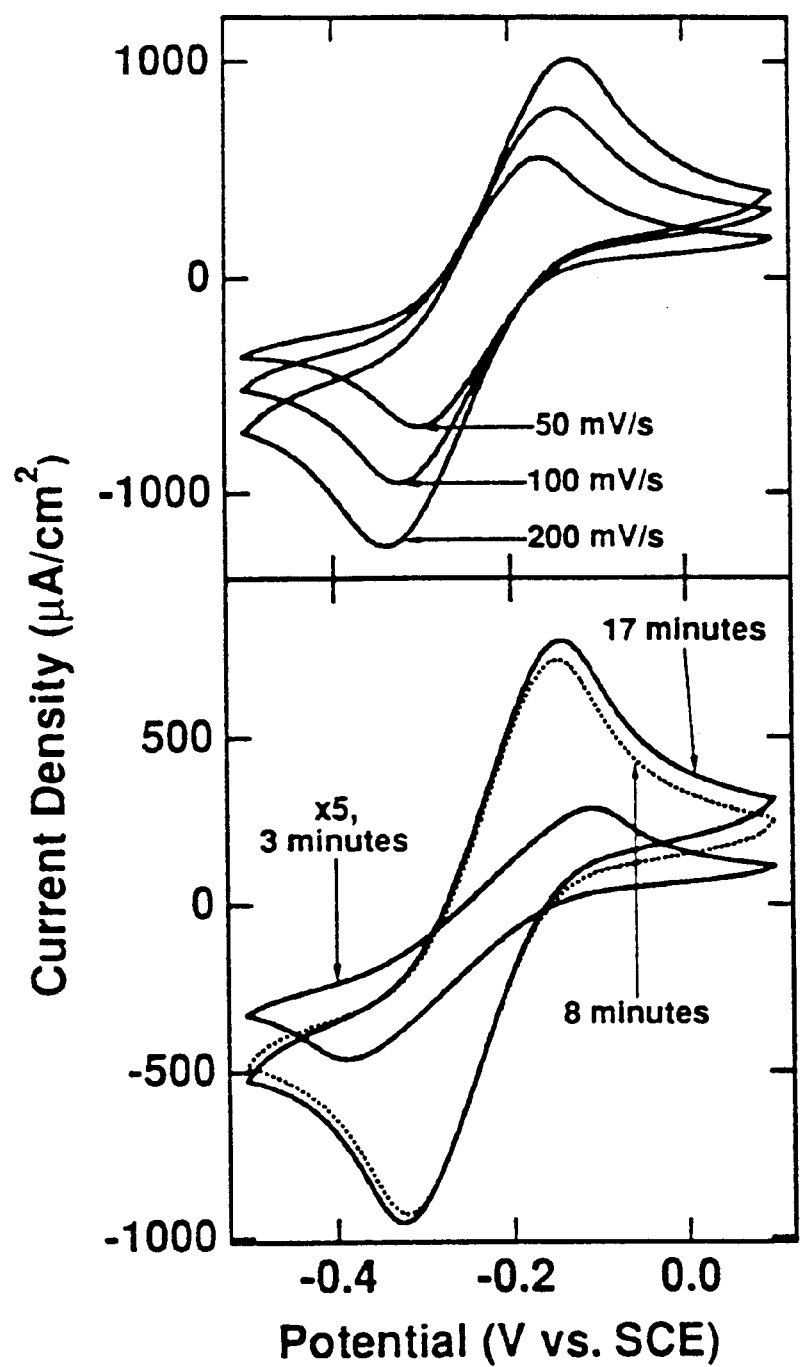
FIG. 9, at the top, shows cyclic voltammograms at three different scan rates of 5 mM [Ru(NH$_3$)$_6$]Cl$_3$/0.1 M Na$_2$SO$_4$ at a colloidal Au film (12-nm diameter colloidal Au monolayer/APTMS/glass immersed in 0.01% HAuCl$_4$/0.4 mM NH$_2$OH in an orbital shaker at 120 rpm for 17 minutes), and, in the bottom panes, shows comparison of 100-mv/s cyclic voltammograms of the same electrolyte taken at colloidal Au monolayers seeded (as above) for 3, 8, and 17 minutes.

Given the high conductivity of these films, they can be used as working electrodes in cyclic voltammetry (CV) experiments; see FIG. 9. The top panel shows cyclic voltammograms for $[Ru(NH_3)_6]^{3+}$ at three different scan rates for a high-coverage, 17-minute seeded Au film. Quasi-reversible voltammetry is obtained, with an $E^{o\prime}$ of –0.23 V vs. SCE, and peak-to-peak separations ($\Delta E_p$) of 135 mV at 50 mV/s, 180 mV at 100 mV/s, and 210 mV at 200 mV/s. The increase in $\Delta E_p$ with increasing scan rate is indicative of one (or more) barriers to heterogeneous electron transfer (ET), among which could include lack of cleanliness of the electrode, poor ET kinetics at films deposited from solution, or barriers due to complex morphology (vide infra). In any case, there is a clear difference between the highly conductive and partially conductive films (bottom panel): the CV for the Au colloid monolayer immersed for three minutes in to 0.01% $HAuCl_4$/0.4 mM $NH_2OH$, the magnitude of the cathodic current is roughly ten-fold smaller than for the highly conductive films; the broad, drawn-out nature of the CV results in large part from the IR drop across the electrode.

The third set of resistance measurements in Table 3 were made on Au colloid multilayers exposed to 0.01% $HAuCl_4$/ 0.4 mM $NH_2OH$ for varying lengths of time. From the resistance data and UV-Vis-near IR spectra, it appears that catalysis of the $Au^{3+}\rightarrow Au^\circ$ reaction is not facile on colloidal Au particles (at least partially) coated with organic adsorbates such as 2-mercaptoethylamine. Even though the initial, four-layer sample had an absorbance of ≈0.4 (i.e. four times as many particles), the sample resistance is higher per unit time than for the high-coverage Au colloid monolayer.

Moreover, although the resistance drops by five orders of magnitude, the near-IR absorbance does not become completely wavelength-independent after 10 minutes of seeding.

Despite these differences, however, the three types of samples discussed in Table 3, namely high- and low-coverage Au colloid monolayers and Au colloid multilayers, all comprise good substrates for $Au^{3+}/NH_2OH$ seeding: all exhibit precipitous decreases in resistance, and all take on bulk optical properties in the near-IR similar to those exhibited by evaporated Au films.

Film Nanostructure by AFM and FE-SEM

While the bulk measurements described above certainly provide evidence that immobilized Au nanoparticles can be enlarged by $Au^{3+}/NH_2OH$ seeding, they do not provide the information on particle size and shape. Likewise, while near-IR and resistance data clearly established differences in the approach to metallic behavior for Au colloid monolayers with high and low particle coverages, they do not yield any insight into the actual mechanism of particle coalescence. Both these issues can be resolved by a combination of AFM and FE-SEM analysis. Both types of measurements are essential, since only FE-SEM reveals the true particle positions and dimensions in the x-y plane, and only AFM can measure film thicknesses in the z-direction.

Figure 10:
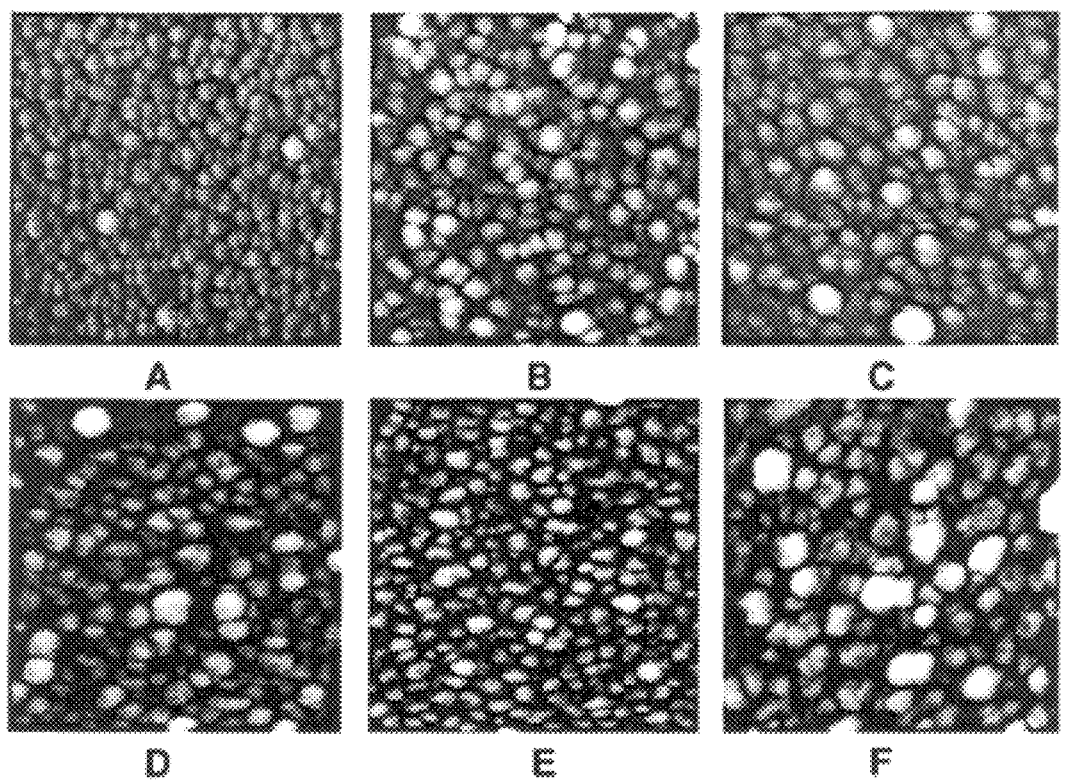
FIG. 10 shows AFM images (1 μm×1 μm) of a 12-nm diameter Au colloid monolayer on MPTMS-coated glass (A), and after shaking in an orbital shaker at 120 rpm in a solution of 0.01% HAuCl$_4$/0.4 mM NH$_2$OH for 3 (B), 6 (C), 7 (D), 9 (E), and 30 minutes (F).
Figure 11:
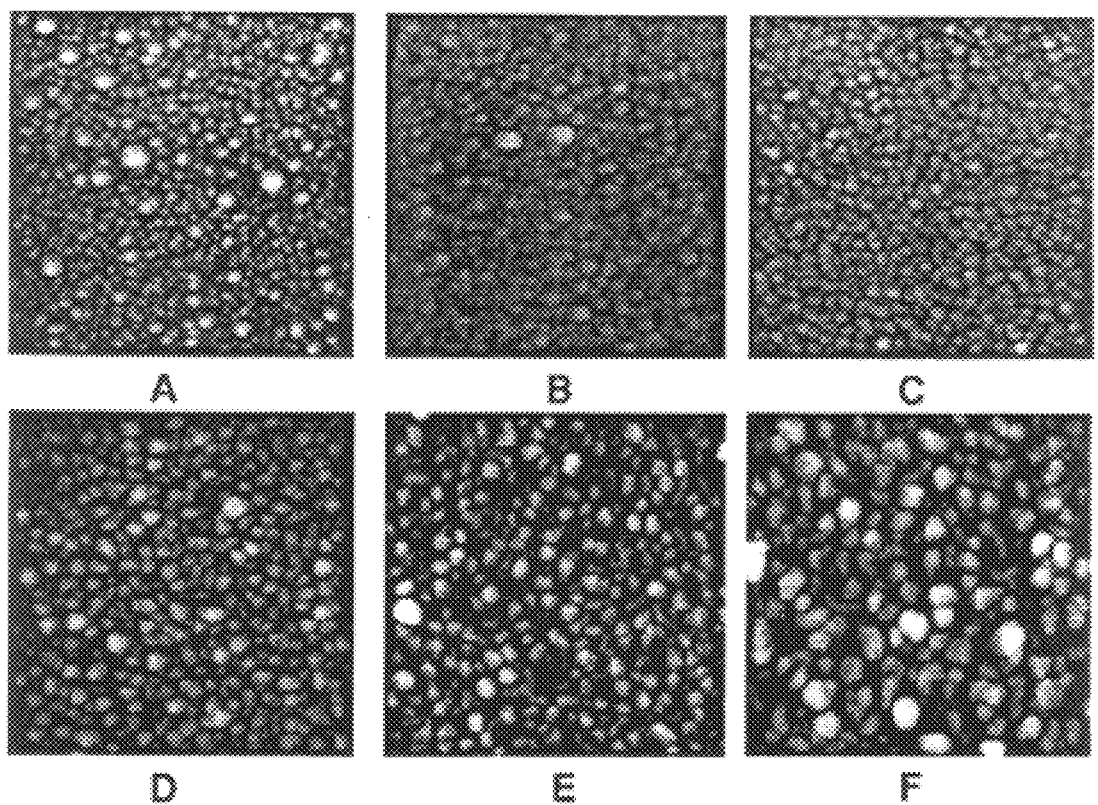
FIG. 11 shows AFM images (1 μm×1 μm) of a 12-nm diameter Au colloid monolayer on APTMS-coated glass (A), and after shaking in an orbital shaker at 120 rpm in a solution of 0.01% HAuCl$_4$/0.4 mM NH$_2$OH for 2 (B), 3 (C), 5 (D), 8 (E), and 17 minutes (F).

The time course of $Au^{3+}/NH_2OH$-mediated enlargement of immobilized Au nanoparticles at low coverage and at high coverage are revealed by AFM images in FIGS. 10 and 11, respectively. Each figure is made up of six images, starting with the monolayer (A), and follows the evolution of highly conductive films over the last five images (B–F). For each, the latter five images were acquired from the same samples from which resistance data were obtained (Table 3).

The AFM image of the low-coverage Au colloid monolayer (FIG. 10, panel A) shows individual particles between 12 and 15 nm in height and with flat spaces in between. The corresponding panel in FIG. 11 shows a close-packed arrangement of particles. This is an artifact of AFM tip convolution on these samples—previous FE-SEM and TEM data have conclusively shown that images such as these correspond to 0.2–0.3 monolayers. Nevertheless, the two images provide a clear view of the differences in initial particle coverage.

For the low-coverage film, $Au^{3+}/NH_2OH$ seeding leads to evolution of features that are both taller and broader. The line scan corresponding to Panel F in FIG. 10 shows features as tall as 50 nm and as wide as 75 nm (the line scan indicates a width of ≈150 nm, but true particle dimensions in the x-y plane are actually only about half those recorded. Moreover, the features are substantially closer together than the original features imaged on the colloidal monolayer. Because of AFM tip convolution, it is impossible to determine interparticle spacing, but it is worth noting that the samples corresponding to images D, E, and certainly F conduct electricity (Table 3). Therefore, there are extensive domains where particles are in contact or are close enough to each other to allow efficient electron tunneling. AFM tip convolution also prevents calculation of the particle ellipticity G, but there appear to be none of the high-aspect ratio rod-shaped particles synthesized during $Au^{3+}/NH_2OH$ seeding in solution.

$Au^{3+}/NH_2OH$ seeding on the high-coverage Au colloid monolayer (FIG. 11) follows a different pattern than that described for the low-coverage sample (FIG. 10). While comparison of Panels A and F clearly indicate an increase in both particle height and width, neither is as dramatic as seen for the low-coverage film. For example, the largest features for the sample imaged in FIG. 11, Panel F (high coverage, 17 min.-seeding) (or any other image of the same surface) is 25 nm, compared to ≈50 nm for the sample imaged in FIG. 10, Panel F (low coverage, 30 min.-seeding) (or any other image of the same surface). At earlier times, the high coverage surface appears even flatter: the most prominent vertical features in line scans of Panels B, C, and D of FIG. 11 are less than 18 nm high.

Short-time seeding of low-coverage Au colloid monolayers leads to a startlingly different (but expected) nanostructure (FIG. 12, panel B): after 6 minutes, there is little particle fusion. To the contrary, a collection of isolated larger particles is seen, many of which are elliptically shaped. Also, about 10–15% of the particles are isolated spheres of 40–50 nm diameter. Clearly, increasing the interparticle spacing promotes "solution-like" enlargement, and notwithstanding the fused particles, the resulting surface looks like one that might be obtained by self-assembly of a 50-nm diameter colloidal Au particles prepared by the Frens method.

FE-SEM images of Au films derived from prolonged $Au^{3+}/NH_2OH$ seeding of high-coverage and low-coverage Au colloid monolayers (panels C and D, respectively, of FIG. 12) are far more similar than their predecessors. Both films exhibit large-scale particle fusion, with all vestiges of the original nanostructure completely obscured. The only discernable difference between the samples is the presence of scattered "holes" in the low-coverage film, likely a product of incomplete coalescence of large particles.

Figure 12:
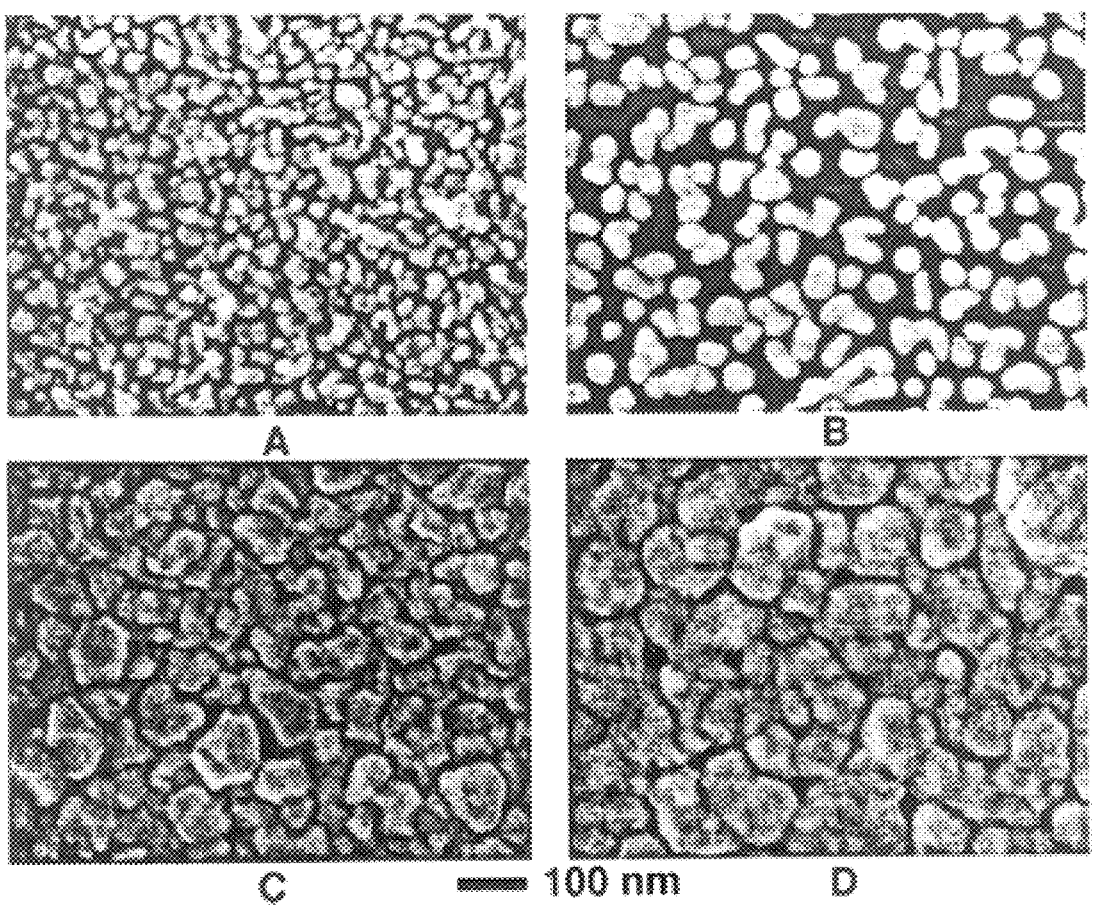
FIG. 12 shows FE-SEM images of Au1/NH$_2$OH-enlarged Au colloid monolayers. Images A and C correspond to samples imaged by AFM in FIG. 11, Panels C and F, respectively; images B and D correspond to samples imaged by AFM in FIG. 10, Panels C and F, respectively.

The images in FIGS. 10–12 reveal how two very different growth mechanisms can yield equally conductive surfaces by $Au^{3+}/NH_2OH$ seeding: at high coverages, early-time coalescence of smaller particles leads to a granular film, while at low coverage, isolated particles are seeded to form distinct, larger particles prior to their ultimate fusion.

Nanometer-Scale Optical Properties

The low transmittance of metallic Au/air interface in the near-IR is an intrinsic optical property of Au that depends solely on its wavelength-dependent dielectric properties. In contrast, several optical properties of Au depend on nanostructure, including SERS, SPR, and non-linear optical behavior. Accordingly, we sought to investigate the effects of particle enlargement and surface roughening via $Au^{3+}/NH_2OH$ seeding on these optical phenomena.

Figure 13:
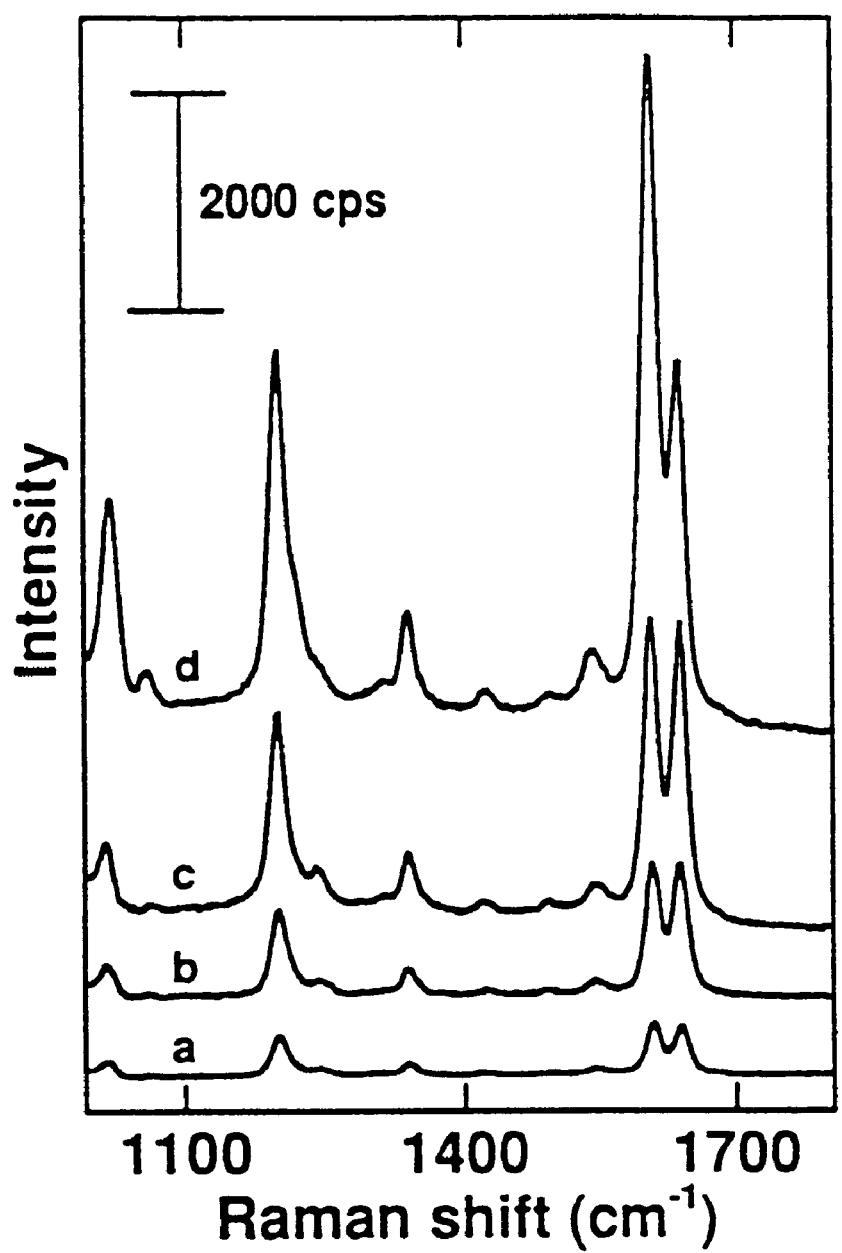
FIG. 13 shows SERS spectra of 10 mM BPE in 9:1H$_2$O:CH$_3$OH drop-coated on 12-nm diameter Au colloid monolayers on APTMS-coated glass as prepared (a) and after exposure to 0.01% HAuCl$_4$/0.4 mM NH$_2$OH for 1 (b), 6 (c) and 17 minutes (d). Acquisition parameters: 23 mW of 632.8-nm photons at the sample, integration time=1 s, ≈8 cm$^{-1}$ bandpass.

FIG. 13 shows SERS spectra for 10 mM solutions of BPE drop-coated onto a 12-nm diameter colloidal Au/APTMS/glass substrate (a) and onto identical substrates after immersion in 0.01% $HAuCl_4$/0.4 mM $NH_2OH$ for 1 (b), 6 (c) and 17 minutes (d). Seeding leads to significant increases in signal (≈50) compared to the relatively weakly enhancing Au colloid monolayer. These surfaces give SERS enhancements equivalent to surfaces prepared by more effort-intensive (and expensive) methods such as evaporation or sputtering.

While SERS is extraordinarily sensitive to nanostructure at the surfaces of free electron metals like Au, it is a rather poor probe of interior nanostructure, as long as it does not impact bulk optical properties. In contrast, SPR depends on propagation of surface plasmons through thin Au films on glass substrates under conditions of total internal reflection. Since the plasmons are launched by evanescent waves that penetrate the Au to a depth of ≈150 nm, internal film structure is critical.

Figure 14:
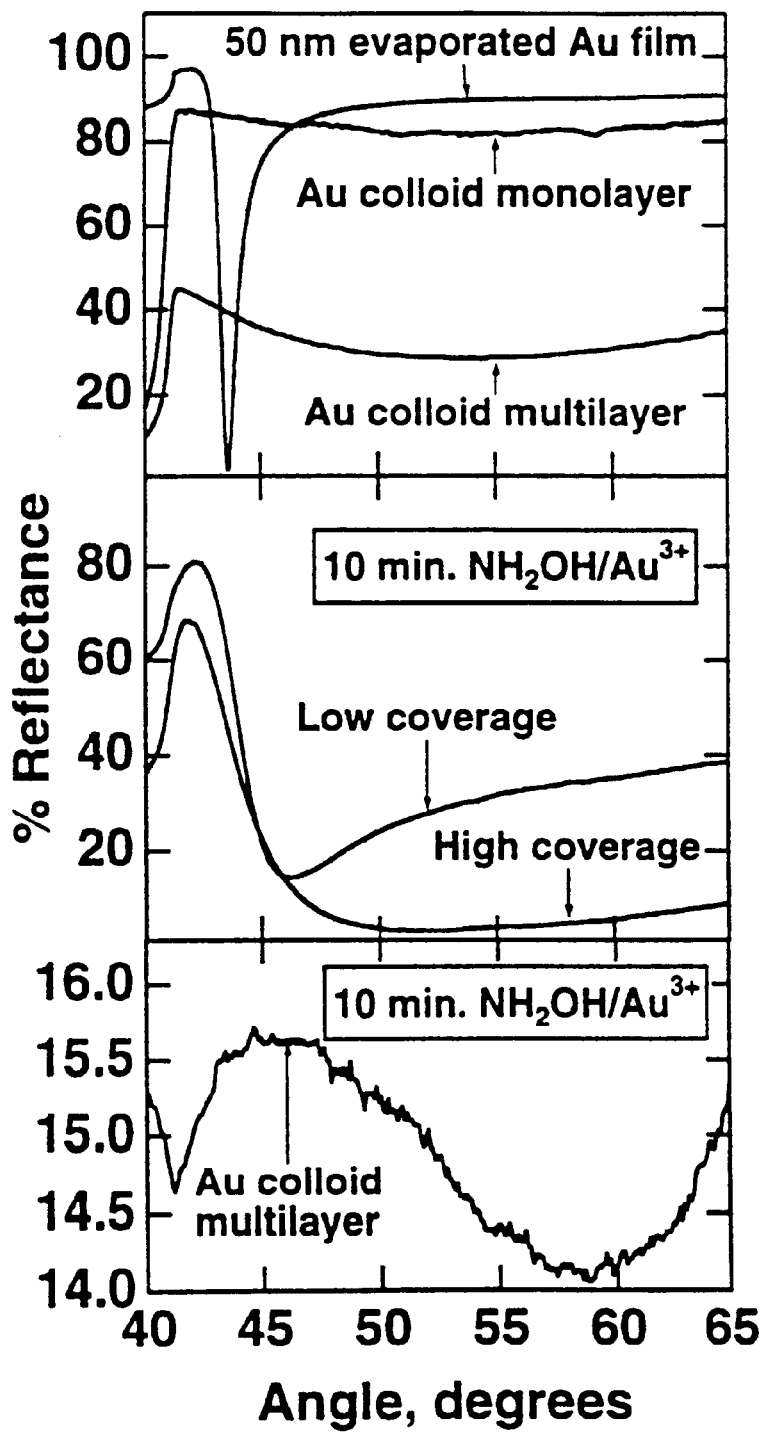
FIG. 14, in the top panel shows a simulated SPR curve for a 50-nm thick evaporated Au film on glass and observed SPR curves for a 12-nm diameter Au colloid monolayer/APTMS/glass substate and a 12-nm diameter Au colloid multilayer substrate (Au colloid monolayer on MPTMS-coated glass with seven additional colloidal layers added using 2-mercaptoethylamine as a bifunctional cross-linker"). The middle panel shows SPR curves for high and low coverage 12-nm diameter Au colloid monolayers on organosilane-coated glass after 10 minutes of shaking in an orbital shaker (at 120 rpm) in a solution of 0.01% HAuCl$_4$/0.4 mM NH$_2$OH. The bottom panel shows SPR curve for the Au colloid multilayer of the top panel after the HAuCl$_4$/NH$_2$OH treatment described for the middle panel.

FIG. 14 shows the variety of SPR responses that can be obtained with evaporated and colloidal Au films. The top panel shows simulated reflectance vs. excitation angle curves for a 50-nm thick evaporated Au film, and experimental data for a 12-nm diameter colloidal Au/APTMS/glass surface and an eight-layer 12-nm diameter Au colloid multilayer. While the evaporated films shows a sharp minimum in reflectivity that comprises the basis for biological applications of SPR, both the Au colloid monolayer and multilayer exhibit broad reflectivity profiles. For the monolayer, the high reflectivity is due to the low sample absorbance at 632.8 nm; the large extinction of the multilayer at this wavelength leads to low reflectivity.

Particle enlargement and/or coalescence by $NH_2OH$ seeding leads to increased definition in SPR reflectivity curves for low- and high-coverage Au colloid monolayers (middle panel) as well as for Au colloid multilayers (bottom panel). For the latter, after a 10-minute immersion in the seeding bath, there is a further decrease in reflectivity, with concomitant evolution of fine structure. In particular, there is a spike at ≈41°, and a sinusoidal variation in reflectivity from 45° to 65°. Changes in reflectivity at the former (the critical angle) are expected; the origin of the latter feature clearly results from changes in film morphology.

Of greater interest are the changes in the monolayer reflectivity after a 10-minute immersion in $Au^{3+}/NH_2OH$. For the high-coverage surface, there is now a broad minimum in reflectivity that only slowly dissipates over 20+°. The low-coverage surface shares a similar profile, but minimum is less shallow. This difference is magnified at 20- and 30-minute immersion times. In general, there is an increase in reflectivity, as expected with 632-nm excitation for Au films that are greater than 50 nm thick. More importantly, while the minimum in reflectivity for the high coverage film is only slightly more pronounced than for a 10-minute immersion, a clean, relatively narrow minimum has evolved on the low-coverage surface. It is surprising that the SPR signature is so dramatically distinct for two films that have the same conductivity (Table 3), the same optical spectrum (FIG. 14), and an almost identical nanostructure (panels C and D of FIG. 12); at the same time, though, it is reasonable to expect that the SPR response, which is ideal for a 50-nm thick Au film with 3–4 nm roughness, would be better on the low-coverage film, in which particle growth proceeded prior to roughly 40–45 nm in diameter prior to coalescence. $Au^{3+}/NH_2OH$ seeding of Au colloid monolayers with even lower coverages would lead to sharper SPR curves, via growth of isolated particles to even larger dimensions before fusion.

$Au^{3+}/NH_2OH$ seeding of colloidal Au films provides entry to a series of complex Au nanostructures that have been probed by UV-Vis near-IR, electrochemistry, resistance measurements, atomic absorption, AFM, FE-SEM, SERS, and SPR. For colloidal Au multilayers linked by 2-mercaptoethylamine, particle enlargement proceeds with the expected consequences, namely increased UV-Vis near-IR extinction, and decreased in resistance and reflectivity. The behavior of Au colloid monolayers depends markedly on particle coverage. At high coverage, seeding leads to early particle coalescence, resulting in films indistinguishable from those prepared by evaporation of Au onto thiol-terminated glass substrates (which is widely used to promote Au adhesion). Indeed, seeding of high-coverage Au colloid monolayers can be considered a vacuum-free route to production of thin films remarkably similar to those produced by evaporation. At low coverage, the isolated particles grow individually into spheres, rods, and ellipses, in analogy to the process in solution. Continued growth leads to conductive films whose reflectivity vs. excitation-angle curves exhibits pronounced minima. Once again, this property resembles that of evaporated Au films of narrowly-defined specifications that are used for SPR experiments.

Methodology to generate films composed of metal nanoparticles assembled in a stepwise fashion entirely from solution is presented; thus, there are few constraints on substrate size or shape. By controlling feature size, spacing, shape, and composition, optical and electrical properties may be tuned. Films assembled using crosslinker, ≦8 Å in length have optical properties and conductivity comparable to their bulk metal counterpart. These were shown to be suitable for use as planar electrodes or SERS substrates. Au volume fractions were shown to be constant at all film heights, close to the critical volume fraction predicted by scaling law for the metal-insulator transition. EFM reveals the presence of conductive and insulating regions consistent with the metal-insulator transition. Film roughness is believed to be responsible for the broad SPR curve observed from multilayer films on Au and glass and contribute to the SERS enhancement for BPE absorbed at Au or Ag nanoparticle assemblies. The fabrication of patterned multilayers with a low error density using microcontact printing and construction of biologically active HRP-linked multilayers provide the groundwork for the development of colloidal nanoparticle devices as biosensor and electronics.

EXAMPLES

General protocols for synthesis, characterization, handling, and storage of colloidal Au solutions—including for 17 nM, 12-nm diameter particles—have been previously described in Grabar, et al., *Anal. Chem.* 1995, 67:735–43; Bright, et al., *Langmuir* 1996, 12:810–17; Freeman, et al., *Science* 1995, 267:1629–32; and Grabar, et al., *Langmuir* 1996, 12:2353–61; each specifically incorporated by reference. $Na_3$ citrate, $NaBH_4$, HCl, $HNO_3$, NaOH, $H_2SO_4$, and aqueous $H_2O_2$ were obtained from J. T. Baker, Sigma-Aldrich, Fisher (Acros), or VWR and used without further purification. 1,6-hexanedithiol, ethylenediaminetetraacetic acid dihydrate, disodium salt (EDTA), $Na_2SO_4$, trans-4,4'-bis-(4-pyridyl)ethylene (BPE), and 2-mercaptoethylamine were purchased from Aldrich. $NH_2OH.HCl$ (henceforth $NH_2OH$) was purchased from Acros or Aldrich. $[Ru(NH_3)_6]Cl_3$ was obtained from Strem Chemicals. 3-aminopropyltrimethoxysilane (APTMS) and 3-mercaptopropyltrimethoxysilane (MPTMS) were purchased from United Chemical Technologies or Aldrich. The following materials were obtained from Sigma: horseradish peroxidase, 2-mercaptoethanol, 2-mercaptoethylamine (MEA). 3-mercaptopropyltrimethoxysilane (MPTMS), and 3-mercaptopropylmethyldimethoxysilane (MPMDMS) were purchased from Gilest. $H_2O$ was purified to ≧18 Ω with a Barnstead Nanopure water purification system. All chemicals were used as received except for BPE, which was recrystallized several times from $CH_3OH/H_2O$. Glass substrates (microscope slides and cover slips) were obtained from VWR or Fisher Scientific Co. and cleaned using protocols previously described in Grabar, et al., *Langmuir,* 1996, 12:2353–61, prior to derivatization.

EXAMPLE 1

Atomic Absorption Spectroscopy

Samples for atomic absorption (AA) were prepared by digesting 0.1 ml of colloidal Au solution with 30 µl of concentrated $HNO_3$ and 30 µl of concentrated HCl, and diluted to 10 ml. 0.1 ml of this solution was mixed with 0.1 ml of 2% $HNO_3$ and 0.8 ml of $H_2O$ for analysis. Standards were prepared from a 100 ppm stock solution of Au ion (Perkin Elmer), from which 0.1 ml was mixed with 0.1 ml of 30 µl $HNO_3$/30 µl HCl and diluted to 10 ml. Different volumes of 1 ppm stock were mixed with 0.1 ml of 2% $HNO_3$ and diluted to 1.0 ml to yield standards between 25 and 200 ppb. AA samples were burned at 130° C. for 60 s, 1000° C. for 45 s, and atomized at 1800° C. with a 5-s reading window. No salt interference was observed.

EXAMPLE 2

2.6 nm-Diameter Colloidal Au 1.00 ml of 1% $HAuCl_4$ was added to 90 ml of $H_2O$ at room temperature (20–23° C.). After one minute of stirring, 2.00 ml of 38.8 mM Na$_3$citrate was added. One minute later, 1.00 ml of fresh 0.075% NaBH$_4$ in 38.8 mM Na$_3$citrate was added. The colloidal solution was stirred for an additional 5 minutes and stored in a dark bottle at 4° C. TEM images of the 2.6-nm diameter colloidal gold particles are shown in FIG. 9.

EXAMPLE 3

Citrate-Seeded Colloidal Au

To a stirred solution of boiling 0.01% HAuCl$_4$, seed colloids (either 2.6-nm diameter or 12-nm diameter) were added coincidentally with the addition of 38.8 mM Na$_3$citrate (final concentration 0.17 mM). This mixture was boiled for 15 minutes and stirred for an additional 10 minutes while cooling. Citrate-seeded colloids were prepared in volumes ranging from 50 ml to 500 ml, with different diameters were generated by changing the volume of seed colloid added.

EXAMPLE 4

NH$_2$OH-Seeded Colloidal Au

These syntheses utilized stock solutions of 1% HAuCl$_4$ and 40 mM H$_2$NOH, diluted to final concentrations as described in the Brief Description of the Figures. Except where noted, seed particles were added to stirred mixtures of NH$_2$OH and HAuCl$_4$.

EXAMPLE 5

Instrumentation for Analysis of Colloidal Metal Nanoparticles

Optical spectra were obtained on an HP8452A diode array UV-Vis spectrophotometer with a deuterium lamp (350–820 nm range, 2 nm resolution). Graphite furnace atomic absorption was performed with a Perkin-Elmer 11008 spectrophotometer, an HGA 700 power supply, an AS-70 autosampler and a Au lamp (Perkin Elmer). Equipment and protocols for acquisition and analysis of transmission electron microscopy (TEM) images have been described in Grabar, et al., *Anal. Chem.* 1995, 67:735–43; Bright, et al., *Langmuir* 1996, 12:810–17; Freeman, et al., *Science* 1995, 267:1629–32; Grabar, et al., *Langmuir* 1996, 12:2353–61; and Grabar, et al., *Anal. Chem.* 1997, 69:471–477; each specifically incorporated by reference. Software protocols that allowed 2-D clusters of particles to be separated into individual entities (or when this was not possible, eliminated from consideration) were employed.

EXAMPLE 6

Film Growth

Colloidal Au nanoparticles measuring 12±1 nm in diameter were prepared, sized by TEM/image analysis, and assembled into 2-D arrays on silanized glass substrates according to methods described in Grabar, et al., *Anal. Chem.* 1995, 67:735–43; Bright, et al., *Langmuir* 1996, 12:810–17 and Freeman, et al., *Science* 1995, 267:1629–32. Au colloid multilayers were made by taking 12-nm diameter colloidal Au monolayers (immobilized on MPTMS-coated glass) and immersing them for 10 minutes in 10 mM 2-mercaptoethylamine. After exhaustive rinsing with H$_2$O the surfaces were immersed in a fresh solution of 17 nM, 12-nm diameter colloidal Au nanoparticles for one hour. This process was repeated between 3–8 times (as indicated in the text).

In brief, hydroxylamine reduced Au metal films were developed on colloidal monolayers in 600 mL of 0.01% HAuCl$_4$/0.4 mM NH$_2$OH on an orbital shaker. The surfaces were dried for optical spectra, conductivity measurements, AFM, FE-SEM and atomic absorbance.

More specifically, reduced Au metal films started from sets of Au colloid monolayers were prepared using either glass microscope slides (cut to 2.5×0.8 cm.) or glass microscope cover slips (2.5×2.5 cm). One side was wiped clean of colloid and the optical spectra were taken of the surface immersed in water. All monolayers were transferred to a solution of NH$_2$OH in an 8 in.×8 in. Pyrex dish and placed on a Lab-Line orbital shaker operated at 120 rpm. A solution of HAuCl$_4$ was added to initiate the reaction. All surfaces were exposed to the same reducing solution; samples were removed at regular intervals for subsequent characterization. After removal, surfaces were immediately washed in water, dried in a stream of Ar gas and stored in vials or Petri dishes. For each surface, an optical spectrum was recorded, after which two electrical contacts were deposited using a Circuit Works conductive pen from Planned Products. When the contacts dried, resistance between the contacts was measured and then the surfaces were imaged by AFM. At least two 5 µm×5 µm scans and eight 1 µm×1 µm images were collected from each surface; for FE-SEM, two 5 µm scans and two 1 µm scans were taken for each surface.

EXAMPLE 7

Instrumentation for Analysis of Colloidal Au Monolayers

Optical spectra were acquired on either an HP8452 UV-Vis connected to a Swan 386 (IBM compatible) or a Perkin-Elmer Lambda 9 spectrophotometer connected to a Gateway 486 (IBM compatible), using software supplied by the manufacturer. Resistance measurements were made with a Fluke 77 multimeter. Atomic absorbance measurements were made using a Perkin Elmer 11008 Graphite Furnace atomic absorption spectrophotometer.

SERS spectra were also collected using a Detection Limited microRaman system which consists of a Solution 633 Helium-Neon laser with a distal probe connected by fiber optic cable. The CCD and data collection were controlled by a Monorail PC clone running DLSPEC software. The lens used had a working distance of 3 mm, resulting in a spot size of approximately 5 µm. The band pass for the microRaman system is ≈8 cm$^{-1}$. Data were processed and analyzed using GRAMS 32 software. Spectra were collected at 632.8 nm. All samples were run at 23 mW with 10-s integration time.

AFM images were acquired using a Digital Instruments Nanoscope IIIa in tapping mode at a frequency of 1–2 Hz, and 512 lines per image using standard Si cantilevers from Digital Instruments. TEM images were taken in a JEOL model 1200EXII operated at 80 kV accelerating voltage and 100K magnification. FE-SEM images were acquired on a JEOL JSM 6320E at 3.0 kV accelerating voltage and 100K magnification.

SPR spectra were obtained on surfaces of dimensions 2.5×2.5 cm with a hemispherical prism (index of refraction 1.515) illuminated by a Spectra-Physics model 127 HeNe gas laser. Data was collected with a Newport photodiode (1 ns rise time) and a Stanford Research optical chopper and 530 lock-in amplifier. The instrument was operated by in-house written Labview 4.0 software operated by a Power Computing PowerCenter 150.

All electrochemical measurements were carried out using a PAR Model 273A Potentiostat/Galvanostat operated with Model 270 Software on a Gateway 486 IBM-compatible computer. All electrochemical measurements were taken in a beaker with the working electrode hanging in solution. Electrochemical solutions consisted of 5 mM [Ru(NH$_3$)$_6$]Cl$_3$ in 0.1 M Na$_2$SO$_4$. The sample was scanned four times with the fourth scan being saved.

TABLE 1

Physical Properties of Colloidal Au Nanoparticles Prepared by Direct Citrate Reduction and By Citrate Seeding of 2.6-nm Diameter and 12-nm Diameter Colloidal Au Solutions

| | Batch | Major Axis × Minor Axis[a] | G[b] | $\lambda_{max}$ (nm) | Peak Width (nm) | Source of Colloid |
|---|---|---|---|---|---|---|
| Small seeds | | 2.6 (1.0) × 2.0 (0.8) | 1.30 | 514 | 104 | this work |
| Large seeds | | 12.6 (1.1) × 11.5 (1.0) | 1.10 | 518 | 84 | this work |
| Synthetic Method | | | | | | |
| Direct Citrate | 1 | 21 (2.3) × 19 (2.3)[c] | 1.13 | 524 | 83 | Goodman |
| | 2 | 22.3 (5.0) × 18.6 (2.4) | 1.20 | 528 | 116 | this work |
| | 3 | 25 (3.3) × 21 (3.3) | 1.19 | 524 | 90 | Goodman |
| | 4 | 31.7 (7.6) × 24.5 (3.9) | 1.29 | 530 | 136 | this work |
| | 5 | 35 (4.0) × 26 (4.0) | 1.33 | 530 | 108 | Goodman |
| | 6 | 44 (6.9) × 33 (6.9) | 1.34 | 528 | 104 | Goodman |
| | 7 | 44.9 (9.5) × 36.4 (5.6) | 1.23 | 524 | 118 | this work |
| | 8 | 48 (10.5) × 37 (10.5) | 1.31 | 535 | 98 | Goodman |
| | 9 | 56 (8.4) × 41 (8.4) | 1.37 | 535 | 147 | Goodman |
| Seeded, Large | 1 | 19.3 (1.7) × 16.4 (1.1) | 1.18 | 520 | 84 | this work |
| | 2 | 21.4 (2.6) × 18.5 (1.9) | 1.16 | 522 | 80 | this work |
| | 3 | 25.0 (2.2) × 21.3 (1.6) | 1.17 | 524 | 80 | this work |
| | 4 | 28.7 (2.6) × 24.3 (2.0) | 1.18 | 526 | 76 | this work |
| | 5 | 31.1 (3.5) × 26.0 (2.4) | 1.20 | 526 | 82 | this work |
| | 6 | 38.4 (4.7) × 31.8 (2.7) | 1.21 | 528 | 78 | this work |
| | 7 | 44.5 (5.8) × 36.8 (4.1) | 1.21 | 530 | 84 | this work |
| | 8 | 53 (4.8) × 43 (3.1) | 1.23 | 534 | 92 | this work |
| | 9 | 64 (6.3) × 51 (3.8) | 1.26 | 545 | 112 | this work |
| | 10 | 72 (9.4) × 54 (5.2) | 1.33 | 542 | 152 | this work |
| | 11 | 76 (11) × 56 (6.0) | 1.36 | 538 | 116 | this work |
| | 12 | 91 (14) × 68 (8.2) | 1.35 | 550 | 220 | this work |
| Seeded, Small | 1 | 35.8 (8.7) × 30.6 (7.3) | 1.17 | 548 | 188 | this work |
| | 2 | 36.4 (5.2) × 29.6 (3.1) | 1.23 | 530 | 96 | this work |
| | 3 | 43.0 (7.8) × 36.8 (6.2) | 1.17 | 534 | 132 | this work |
| | 4 | 53 (5.2) × 44 (3.7) | 1.21 | 542 | 108 | this work |
| | 5 | 56 (7.2) × 45 (4.6) | 1.25 | 544 | 144 | this work |
| | 6 | 61 (10) × 49 (7.5) | 1.24 | 548 | 164 | this work |
| | 7 | 75 (17) × 60 (11) | 1.24 | 548 | 216 | this work |
| | 8 | 93 (20) × 68 (11) | 1.37 | 572 | 300 | this work |
| | 9 | 108 (38) × 77 (20) | 1.40 | 548 | 300 | this work |
| | 10 | 111 (27) × 81 (17) | 1.38 | 616 | 404 | this work |

[a]Values in parentheses are standard deviations; all values are in nm.
[b]Ellipticity, as defined in test.
[c]Grabar et al., Anal. Chem. 1997, 69:471–477, gives a single standard deviation for a given preparation of particles, so it is used for both axes.

TABLE 2

Particle Size and Shape Analysis for Iteratively NH₂OH-Seeded Colloidal Au Nanoparticles

| FIG. 6 Panel[a] | Number Sized | Mean d Major × Minor[b,c] | Median d[c] Major × Minor | G (Mean) | Predicted Size[c,d] Major × Minor |
|---|---|---|---|---|---|
| Total[e] | | | | | |
| A | 1322 | 13.0 (1.4) × 11.8 (1.2) | 12.8 × 11.7 | 1.10 | |
| B | 2829 | 18.0 (2.7) × 16.3 (2.3) | 17.8 × 16.1 | 1.10 | |
| C | 2263 | 35.1 (9.0) × 28.4 (3.6) | 32.8 × 28.6 | 1.24 | |
| D | 3363 | 51.1 (28.6) × 36.1 (5.4) | 41.7 × 37.0 | 1.42 | |
| E | 917 | 65.8 (31.0) × 49.5 (7.0) | 56.0 × 49.9 | 1.33 | |
| F[f] | g | g | g | g | |
| Spheres | | | | | |
| A | 1183 | 12.9 (1.3) × 11.9 (1.2) | 12.7 × 11.7 | 1.08 | |
| B | 2630 | 17.9 (2.5) × 16.4 (2.3) | 17.7 × 16.2 | 1.09 | 21.0 × 19.0 |
| C | 1964 | 32.4 (3.2) × 29.2 (2.7) | 32.3 × 29.0 | 1.11 | 33.7 × 30.3 |
| D | 2839 | 41.1 (4.0) × 37.7 (3.5) | 41.0 × 37.6 | 1.09 | 45.5 × 41 |
| E | 799 | 56.2 (5.4) × 51.0 (5.1) | 55.3 × 50.4 | 1.10 | 59 × 53 |
| F | 1443 | 116 (11) × 102 (10) | 116 × 102 | 1.14 | 121 × 103 |
| Rods[e] | | | | | |

TABLE 2-continued

Particle Size and Shape Analysis for Iteratively
NH₂OH-Seeded Colloidal Au Nanoparticles

| FIG. 6 Panel[a] | Number Sized | Mean d Major × Minor[b,c] | Median d[c] Major × Minor | G (Mean) | Predicted Size[c,d] Major × Minor |
|---|---|---|---|---|---|
| A | 120 | 14.2 (2.1) × 11.6 (1.7) | 13.7 × 11.2 | 1.22 | |
| B | 100 | 20.8 (4.3) × 15.1 (1.9) | 19.8 × 14.8 | 1.38 | |
| C | 200 | 58.9 (12.8) × 21.4 (3.2) | 57.3 × 21.0 | 2.75 | |
| D | 399 | 122 (32.2) × 25.3 (3.9) | 127.0 × 24.6 | 4.82 | |
| E | 80 | 145 (42.4) × 35.0 (7.0) | 163.5 × 33.0 | 4.14 | |
| F | 200 | 236 (60.3) × 77.1 (9.6) | 233.6 × 74.2 | 3.06 | |

[a]For convenience, solutions of seeded particles have been named according to their TEM image in FIG. 6.
[b]Numbers in parentheses refer to standard deviations.
[c]In nanometers.
[d]With the exception of B, whose predicted size was based on the actual size of A, predictions were based on predicted sizes from the previous iteration.
[e]"Total" refers to all the particles in a given batch of colloid, while "spheres" and "rods" refer those subsets of particles possessing the corresponding shapes. Particles with G>1.2 were called rods.
[f]F represents a two-step iteration from E. The predicted dimensions for the hidden iteration (E') was 84 × 72 nm.
[g]The pronounced bimodality of the particle size distribution precluded meaningful calculation of mean diameter and ellipticity.

TABLE 3

Resistance of Au³⁺/NH₂OH-Seeded Au Colloid Monolayers

| Sample | Immersion Time (Minutes)[a] | Resistance(Ω)[b] | Corresponding AFM Image |
|---|---|---|---|
| Low coverage Au monolayer[c] | 1 | insulating | |
| | 3 | insulating | FIG. 10, Panel B |
| | 6 | 650,000 | FIG. 10, Panel C |
| | 7 | 370 | FIG. 10, Panel D |
| | 8 | 120 | |
| | 9 | 40 | FIG. 10, Panel E |
| | 30 | 4 | FIG. 10, Panel F |
| High coverage Au monolayer[d] | 1 | insulating | |
| | 2 | insulating | FIG. 11, Panel B |
| | 3 | 1000 | FIG. 11, Panel C |
| | 4 | 100 | |
| | 5 | 56 | FIG. 11, Panel D |
| | 6 | 14 | |
| | 8 | 5.6 | FIG. 11, Panel E |
| | 17 | 0.5 | FIG. 11, Panel F |

[a]In a 120 rpm orbital shaker loaded with 0.01% HAuCl₄/0.4 mM NH₂OH.
[b]DC resistance as measured with a two-point probe. Measurement length was 2.1 ± 0.1 cm; sample width was 0.9 ± 0.1 cm.
[c]12-nm diameter Au/MPTMS/glass.
[d]12-nm diameter Au/MPTMS/glass.

What is claimed is:

1. A method for performing surface-enhanced Raman spectroscopy (SERS), comprising:
   a) preparing a substrate by a method comprising:
      i) providing a gold colloid monolayer;
      ii) contacting said gold colloid monolayer with a solution comprising a reductant; and
      iii) contacting said gold colloid monolayer with a solution comprising a source of gold ions;
   b) coating a region of said substrate with an analyte; and
   c) acquiring a SERS spectrum of said analyte on said substrate.

2. The method of claim 1, wherein said reductant is NH₂OH.

3. The method of claim 1, wherein steps (ii) and (iii) are conducted at room temperature.

4. The method of claim 1, wherein said gold colloid monolayer comprises gold nanoparticles with diameters of between about 10 nm and about 15 nm.

5. The method of claim 1, wherein said solution comprising a source of gold ions has a concentration of gold ions selected in dependence on a desired particle size enlargement of said gold colloid monolayer.

6. The method of claim 1, wherein a density of nanoparticles in said gold colloid monolayer is selected in dependence on a desired thickness of said SERS substrate.

7. The method of claim 1, wherein said gold colloid monolayer has a coverage of approximately 20%.

8. A method for performing surface-enhanced Raman spectroscopy (SERS), comprising:
   a) obtaining a substrate prepared by a method comprising:
      i) providing a gold colloid monolayer;
      ii) contacting said gold colloid monolayer with a solution comprising a reductant; and
      iii) contacting said gold colloid monolayer with a solution comprising a source of gold ions;
   b) coating a region of said substrate with an analyte; and
   c) acquiring a SERS spectrum of said analyte on said substrate.

* * * * *